United States Patent
Shi et al.

(10) Patent No.: US 10,573,827 B2
(45) Date of Patent: Feb. 25, 2020

(54) ORGANIC METAL COMPLEX, AND POLYMER, MIXTURE, COMPOSITION AND ORGANIC ELECTRONIC DEVICE CONTAINING SAME AND USE THEREOF

(71) Applicant: GUANGZHOU CHINARAY OPTOELECTRONIC MATERIALS LTD., Guangzhou (CN)

(72) Inventors: Chao Shi, Guangzhou (CN); Junyou Pan, Guangzhou (CN)

(73) Assignee: GUANGZHOU CHINARAY OPTOELECTRONICS MATERIALS LTD., Guangzhou (CN)

( * ) Notice: Subject to any disclaimer, the term of this patent is extended or adjusted under 35 U.S.C. 154(b) by 0 days.

(21) Appl. No.: 15/535,021

(22) PCT Filed: Dec. 11, 2015

(86) PCT No.: PCT/CN2015/097188
§ 371 (c)(1),
(2) Date: Dec. 11, 2017

(87) PCT Pub. No.: WO2016/091217
PCT Pub. Date: Jun. 16, 2016

(65) Prior Publication Data
US 2018/0130961 A1    May 10, 2018

(30) Foreign Application Priority Data
Dec. 11, 2014    (CN) .......................... 2014 1 0766889

(51) Int. Cl.
| H01L 51/00 | (2006.01) |
| C07F 15/00 | (2006.01) |
| C09K 11/06 | (2006.01) |
| H01L 51/50 | (2006.01) |

(52) U.S. Cl.
CPC ...... H01L 51/0085 (2013.01); C07F 15/0033 (2013.01); C07F 15/0086 (2013.01); C09K 11/06 (2013.01); H01L 51/0087 (2013.01); C09K 2211/1029 (2013.01); C09K 2211/1044 (2013.01); C09K 2211/1059 (2013.01); C09K 2211/185 (2013.01); H01L 51/5016 (2013.01); H01L 2251/552 (2013.01)

(58) Field of Classification Search
None
See application file for complete search history.

(56) References Cited

U.S. PATENT DOCUMENTS

| 3,563,450 A | 2/1971 | Dahlberg |
| 3,567,450 A | 3/1971 | Grantly et al. |
| 3,615,404 A | 10/1971 | Mattor et al. |
| 4,720,432 A | 1/1988 | Vanslyke et al. |
| 4,769,292 A | 9/1988 | Tang et al. |
| 5,015,669 A | 5/1991 | Aumann et al. |
| 5,061,569 A | 10/1991 | Vanslyke et al. |
| 5,121,029 A | 6/1992 | Hosokawa et al. |
| 5,130,603 A | 7/1992 | Tokailin et al. |
| 6,020,078 A | 2/2000 | Chen et al. |
| 6,251,531 B1 | 6/2001 | Enokida et al. |
| 7,250,226 B2 | 7/2007 | Tokito et al. |
| 7,250,532 B2 | 7/2007 | Iwakuma et al. |
| 7,767,317 B2 | 8/2010 | Begley et al. |
| 2004/0002576 A1 | 1/2004 | Oguma et al. |
| 2004/0076853 A1 | 4/2004 | Jarikov |
| 2006/0210830 A1 | 9/2006 | Funahashi et al. |
| 2006/0222886 A1 | 10/2006 | Kwong et al. |
| 2007/0087219 A1 | 4/2007 | Ren et al. |
| 2007/0092753 A1 | 4/2007 | Begley et al. |
| 2007/0208567 A1 | 9/2007 | Amento et al. |
| 2007/0252517 A1 | 11/2007 | Owczarczyk et al. |
| 2008/0113101 A1 | 5/2008 | Inoue et al. |
| 2009/0134784 A1 | 5/2009 | Lin et al. |
| 2013/0032766 A1* | 2/2013 | Molt ................... C07F 15/0033 252/519.2 |
| 2014/0027716 A1 | 1/2014 | Tsai et al. |

FOREIGN PATENT DOCUMENTS

| CN | 1583691 A | 2/2005 |
| CN | 1751055 A | 3/2006 |

(Continued)

OTHER PUBLICATIONS

State IP Office of P.R. China; International Search Report for counterpart International Application No. PCT/CN2015/097188 containing International Search Report in English, 6 pgs, (dated Mar. 17, 2016).
State IP Office of P.R. China; Written Opinion for counterpart International Application No. PCT/CN2015/097188, 4 pgs, (dated Mar. 17, 2016).
Newkome, George R., et al.; "Dendrimers and Dendrons—Concept, Syntheses, Applications"; Wiley-VCH Verlag GmbH & Co. KGaA (2002); 320 pp.
Bulovic, V. et al., "Transparent Light-Emitting Devices." Nature, Mar. 1996; 380(29); p. 29.

(Continued)

Primary Examiner — Katie L. Hammer
(74) Attorney, Agent, or Firm — Womble Bond Dickinson (US) LLP

(57) ABSTRACT

An organic metal complex as shown by general formula (I) or (II), wherein the ring containing $Ar^1$ is preferably a N-hetero six-membered aromatic ring, and a polymer, a mixture, a composition and an organic electronic device comprising the complex and a use thereof. The organic electronic device, particularly an organic light emitting diode, and the use thereof in display and illumination technologies. By optimizing the device structure and changing the concentration of the metal complex in a matrix, the best performances of the device can be attained, an OLED device with a high efficiency, high luminance and high stability is achieved, and a relatively good material option is provided for full-colour display and illumination applications.

19 Claims, No Drawings

(56) References Cited

FOREIGN PATENT DOCUMENTS

| | | |
|---|---|---|
| DE | 102004020298 A1 | 11/2005 |
| DE | 102005058557 A1 | 6/2007 |
| DE | 102009023156 A1 | 12/2010 |
| DE | 102009023154 A1 | 6/2011 |
| EP | 1344788 B1 | 9/2003 |
| EP | 1345477 A2 | 9/2003 |
| EP | 1144543 B1 | 3/2004 |
| EP | 1957606 A1 | 8/2008 |
| EP | 1941562 B1 | 5/2010 |
| EP | 2730583 A1 | 5/2014 |
| EP | 2743274 A1 | 6/2014 |
| EP | 3172004 A1 | 5/2017 |
| JP | 2913116 B2 | 6/1999 |
| JP | 2003338375 A | 11/2003 |
| JP | 2005108556 A | 4/2005 |
| JP | 2005285661 A | 10/2005 |
| JP | 2007059939 A | 3/2007 |
| JP | 2007197574 A | 8/2007 |
| JP | 2007211243 A | 8/2007 |
| JP | 2008053397 A | 3/2008 |
| WO | 0121729 A1 | 3/2001 |
| WO | 03020790 A2 | 3/2003 |
| WO | 03051092 A1 | 6/2003 |
| WO | 03099901 A1 | 12/2003 |
| WO | 2004041901 A1 | 5/2004 |
| WO | 2004113412 A2 | 12/2004 |
| WO | 2005033174 A1 | 4/2005 |
| WO | 2005056633 A1 | 6/2005 |
| WO | 2005104264 A1 | 11/2005 |
| WO | 2006000388 A1 | 1/2006 |
| WO | 2006000389 A1 | 1/2006 |
| WO | 2006052457 A2 | 5/2006 |
| WO | 2006058737 A1 | 6/2006 |
| WO | 2006062226 A1 | 6/2006 |
| WO | 2006114364 A1 | 11/2006 |
| WO | 2006118345 A1 | 11/2006 |
| WO | 2006122630 A1 | 11/2006 |
| WO | 2007043495 A1 | 4/2007 |
| WO | 2007065549 A1 | 6/2007 |
| WO | 2007065678 A1 | 6/2007 |
| WO | 2007115610 A1 | 10/2007 |
| WO | 2007140847 A1 | 12/2007 |
| WO | 2008006449 A1 | 1/2008 |
| WO | 2010135519 A1 | 11/2010 |
| WO | 2011110277 A1 | 9/2011 |
| WO | 2011141110 A2 | 11/2011 |
| WO | WO 2012/162488 A1 | 11/2012 |

OTHER PUBLICATIONS

Gu, G., et al., "Transparent Organic Light Emitting Devices." Appl. Phys. Lett., May 1996; 68(19), pp. 2606-2608.

Kipphan, H., "Handbook of Print Media: Technologies and Production Methods," Springer, Feb. 27, 2014, ISBN 3-540-67326-1, 1207 pages.

* cited by examiner

ORGANIC METAL COMPLEX, AND POLYMER, MIXTURE, COMPOSITION AND ORGANIC ELECTRONIC DEVICE CONTAINING SAME AND USE THEREOF

TECHNICAL FIELD

The present disclosure relates to an organic metal complex containing N-hetero-six-membered ring as a new ligand, and a polymer, a mixture, a formulation, an organic electronic device comprising the same and application thereof. In addition, the present disclosure further relates to an organic electronic device comprising the organic metal complex, in particular to an organic light emitting diode, and its use in display and lighting technology.

BACKGROUND

Organic light-emitting diode (OLED) has showed great potential in applications of optoelectronic devices (such as flat-panel displays and lighting) because of the synthetic diversity, relatively low manufacturing costs, and excellent optical and electrical properties of organic semiconductive materials.

In order to improve the emitting efficiency of organic light-emitting diode, various light emitter materials based on fluorescent and phosphorescent materials have been developed. Organic light-emitting diodes using fluorescent materials are characterized by high reliability, but their internal electroluminescence quantum efficiency is limited to 25% under electric field excitation, since the probability ratio of the exciton to singlet excited state and triplet excited state is 1:3. In 1999, Professor Thomson of the University of Southern California and Professor Forrest of Princeton University incorporated tris (2-phenylpyridine) iridium Ir (ppy)$_3$ into N, N-dicarbazole biphenyl (CBP), to successfully prepare green electroluminescent devices, which aroused great interest in complex phosphorescent materials. The introduction of heavy metals improves the molecular spin orbit coupling, shortens the phosphorescence life and enhances the intersystem crossing of molecules, so that phosphorescence can be successfully launched. Further reactions of this kind of complex are mild, thus it is easy to change the complex structure and the substituent group, to adjust the emission wavelength, and thus get the excellent performance of the electroluminescent material. So far, the internal quantum efficiency of phosphorescent OLED is close to 100%. However, the stability of phosphorescent OLED needs to be improved. The stability of the phosphorescent OLED depends largely on the luminous body itself. Most of the widely used iridium and platinum metal complexes are mostly confined to the five-membered ring ligands, while the six-membered ring ligands with structural stability are less. In order to further improve the material properties and broaden the phosphorescent metal complexes, it is urgently needed to develop highly efficient phosphorescent metal complexes containing new ligands.

SUMMARY

In view of the above-mentioned deficiencies of the prior art, it is an object of the present disclosure to provide an N-hetero-six-membered ring organic metal complex, which can effectively improve the stability of the complex material, luminous efficiency and the performance of the corresponding device since the six-membered ring ligands have excellent rigidity, chemical and thermal stability.

A technical solution for achieving the above object is an organic metal complex having a structure of the general formula (I) or (II):

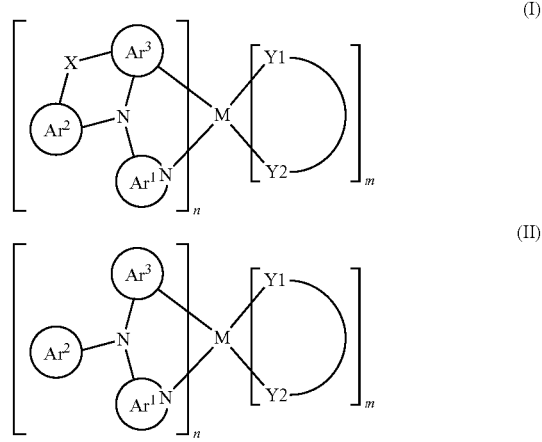

wherein,

X is a bridging group, and when n>1, each X is the same or different bridging group, X being linked to Ar$^3$ or Ar$^2$ by a single bond or a double bond, and X is selected from the group consisting of a single bond, N(R$^1$), B(R$^1$), C(R$^1$)$_2$, O, Si(R$^1$)$_2$, C=C(R$^1$)$_2$, S, S=O, SO$_2$, P(R$^1$) and P(=O)R$^1$;

each R$^1$ is the same or different from one another in multiple occurrences, and R$^1$ is selected from the group consisting of H; F; Cl; Br; I; D; CN; NO$_2$; CF$_3$; B(OR$^2$)$_2$; Si(R$^2$)$_3$; straight-chain alkanes; alkane ethers; alkane thioethers, branched alkanes or cycloalkanes containing 1 to 10 carbon atoms; and alkane ethers or alkane thioether groups containing 3 to 10 carbon atoms; each R$^1$ group is substituted with one or more active groups R$^2$, and one or more non-adjacent methylene groups (CH$_2$) are optionally substituted by any one selected from the group consisting of R$^2$C=CR$^2$, C=C, Si(R$^2$)$_2$, Ge(R$^2$)$_2$, Sn(R$^2$)$_2$, C=O, C=S, C=Se, C=N(R$^2$), O, S, —COO— and CONR$^2$; wherein one or more H can be substituted by D, F, Cl, Br, I, CN or N$_2$; or by an aromatic amine substituted by one or more R$^2$ or one aromatic group or heteroaromatic group; or by a substituted or unsubstituted carbazole.

Each R$^2$ is the same or different from each other in multiple occurrences, and is selected from the group consisting of H, D, an aliphatic alkane having 1 to 10 carbons atoms, an aromatic hydrocarbon, and a substituted or unsubstituted aromatic ring or heteroaromatic group having 5 to 10 carbon atoms.

Each of Ar$^1$-Ar$^3$ is the same or different from each other in multiple occurrence, and is an unsubstituted or a R$^1$-substituted aromatic hydrocarbon or heteroaromatic cylic hydrocarbon system;

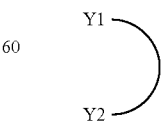

is a bidentate ligand.

M is a transitional metal element.

m and n are respectively any one of numbers 1-3.

In some embodiments, the organic metal complex is preferably selected from the following general formulas:

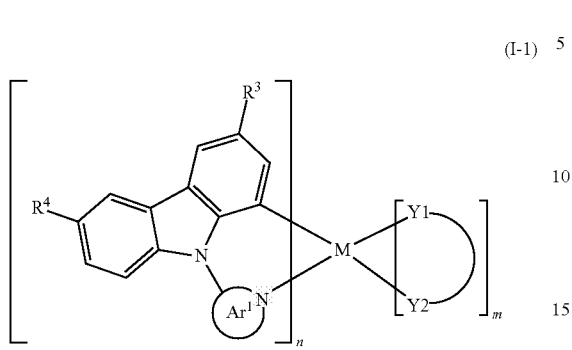
(I-1)

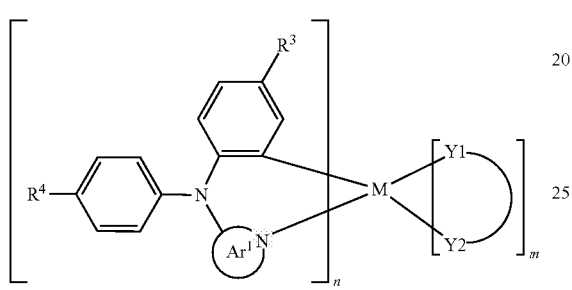
(II-1)

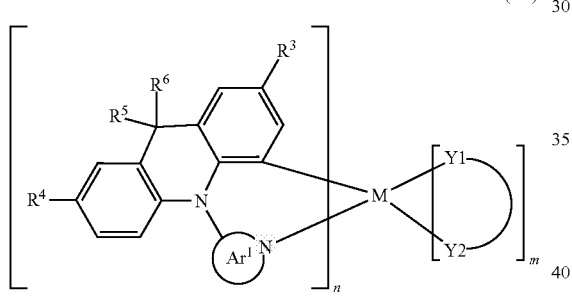
(I-2)

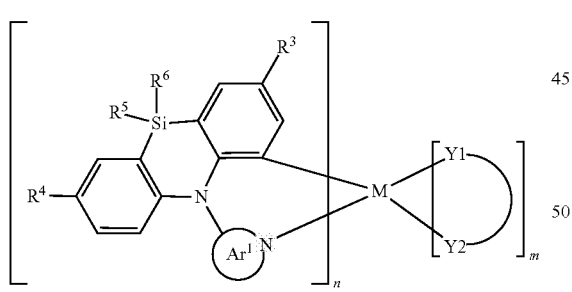
(I-3)

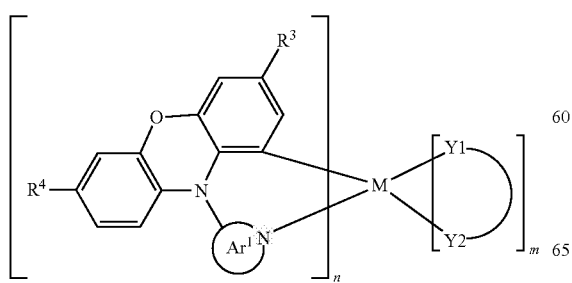
(I-4)

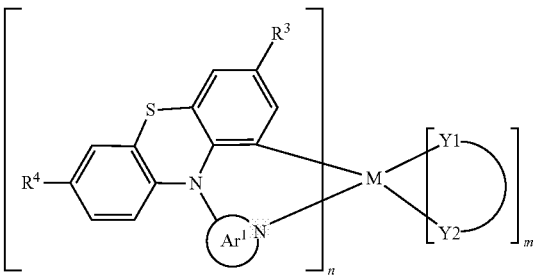
(I-5)

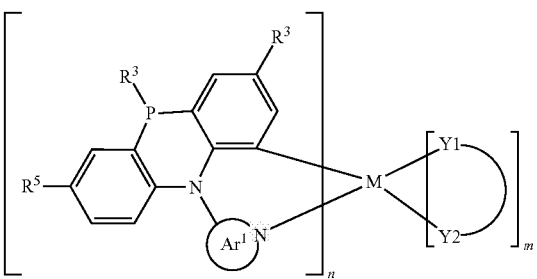
(I-6)

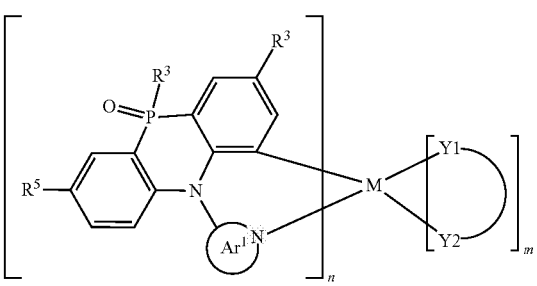
(I-7)

wherein each of $R^3$, $R^4$, $R^5$ and $R^6$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane, or cycloalkane containing 1 to 10 carbon atoms; alkane ether or alkane thioether group containing 3 to 10 carbon atoms; and aryl group containing 6 to 10 carbon atoms.

In some embodiments, M is selected from any one transition metal of the group consisting of Cr, Mo, W, Ru, Rh, Ni, Ag, Cu, Zn, Pd, Au, Os, Re, Ir and Pt. In a preferred embodiment, M is selected from Ir or Pt.

In some embodiment, is N-hetero-six-membered ring unit, and is independently selected from general formulas C1 to C4 in multiple occurrences:

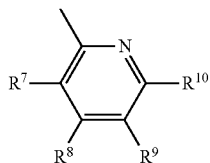 C1

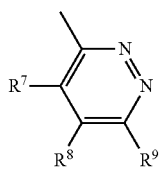 C2

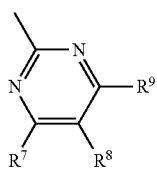 C3

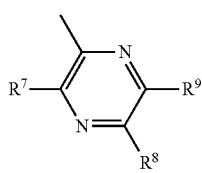 C4

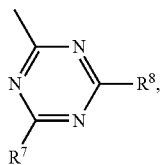 C5 wherein each of $R^7$ to $R^9$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane or cycloalkane containing 1 to 10 carbon atoms; alkane ether or alkane thioether group containing 3 to 10 carbon atoms, and aryl group containing 6 to 10 carbon atoms.

In some embodiments,

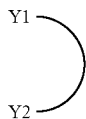

is a single anion ligand, and is independently selected from the following general formulas L1 to L15 in multiple occurrences:

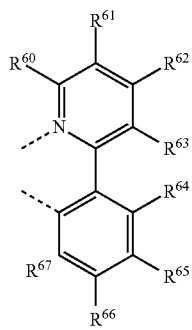 L1

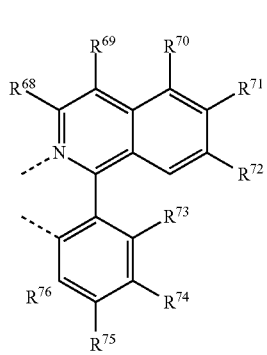 L2

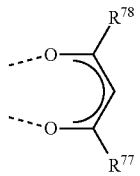 L3

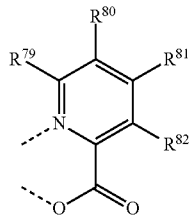 L4

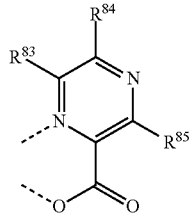 L5

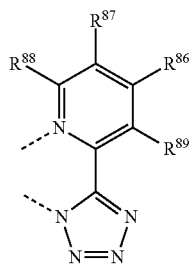 L6

L7 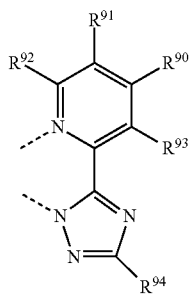

L8 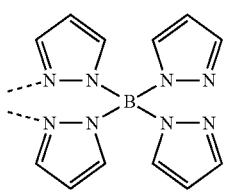

L9 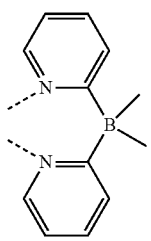

L10 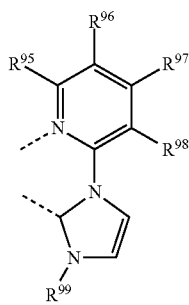

L11 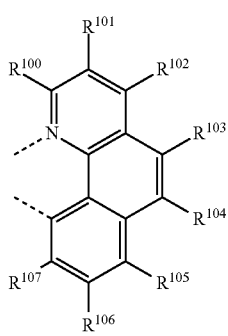

L12 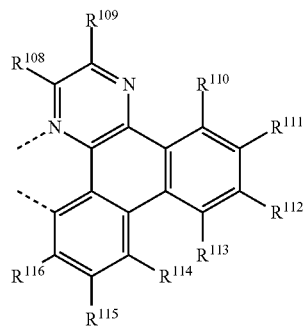

L13 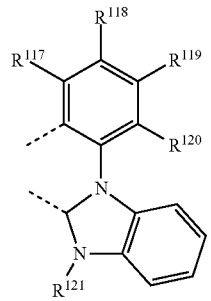

L14 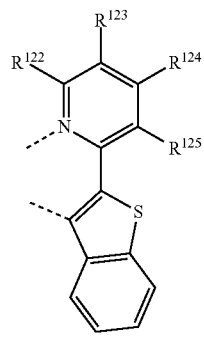

L15 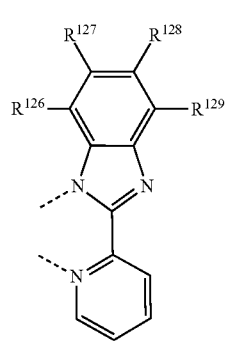

wherein each of $R^{60}$ to $R^{129}$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane or cycloalkane containing 1 to 10 carbon atoms; alkane ether or alkane thioether group containing 3 to 10 carbon atoms, and aryl group containing 6 to 10 carbon atoms, wherein the dashed line indicates connecting with the metal element M in the form of a single bond.

Another object of the present disclosure is to provide a polymer comprising a repeating unit containing a structural unit represented by the general formula (I) or (II).

Another object of the present disclosure is to provide a mixture comprising the organic metal complex of the present disclosure and at least one organic functional material. The organic functional material can be any one selected from the group consisting of a hole-injecting material, a hole-transporting material, an electron-transporting material, an electron-injecting material, an electron-blocking material, a hole-blocking material, a light emitter material, and a host material etc.

Another object of the present disclosure is to provide a formulation comprising the organic metal complex or the polymer, and at least one organic solvent.

Another object of the present disclosure is to provide an use of the organic metal complex in an organic electronic device.

Another object of the present disclosure is to provide an organic electronic device comprising the organic metal complex or the polymer or the mixture thereof.

In some embodiments, the organic electronic device is any one selected from the group consisting of: organic light emitting diode (OLED), organic photovoltaic cell (OPV), organic light emitting electrochemical cell (OLEEC), organic field effect transistor (OFET), organic light emitting field effect transistor, organic laser, organic spintronic device, organic sensor and organic plasmonic emitter diode.

DETAILED DESCRIPTION OF THE EMBODIMENTS

The present disclosure provides an organic metal complex containing N-hetero-six-membered ring and corresponding organic mixture, and application in the organic electronic device. The present disclosure will now be described in greater detail so that the purpose, technical solutions, and technical effects thereof are more clear and comprehensible. It is to be understood that the specific embodiments described herein are merely illustrative of, and are not intended to limit, the disclosure.

The present disclosure relates to an organic metal complex represented by the following general formula (I) or (II):

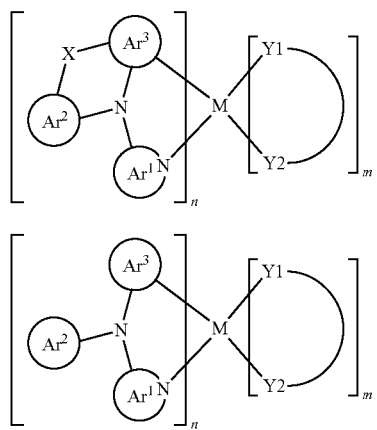

Wherein, X is the same or different bridging group in each occurrence, and they are linked to $Ar^1$ or $Ar^2$ by a single bond or a double bond, and selected from the group consisting of a single bond, $N(R^1)$, $B(R^1)$, $C(R^1)_2$, O, $Si(R^1)_2$, $C=C(R^1)_2$, S, S=O, $SO_2$, $P(R^1)$ and $P(=O)R^1$;

each $R^1$ is the same or different from one another in multiple occurrences, and $R^1$ is selected from the group consisting of H; F; Cl; Br; I; D; CN; $NO_2$; $CF_3$; $B(OR^2)_2$; $Si(R^2)_3$; straight-chain alkanes; alkane ethers; alkane thioethers, branched alkanes or cycloalkanes containing 1 to 10 carbon atoms; and alkane ethers or alkane thioether groups containing 3 to 10 carbon atoms; each $R^1$ group is substituted with one or more active groups $R^2$, and one or more non-adjacent methylene groups ($CH_2$) are optionally substituted by any one selected from the group consisting of $R^2C=CR^2$, $C=C$, $Si(R^2)_2$, $Ge(R^2)_2$, $Sn(R^2)_2$, $C=O$, $C=S$, $C=Se$, $C=N(R^2)$, O, S, —COO— and $CONR^2$; wherein one or more H can be substituted by D, F, Cl, Br, I, CN or $N_2$; or by an aromatic amine substituted by one or more $R^2$ or one aromatic group or heteroaromatic group; or by a substituted or unsubstituted carbazole.

Each $R^2$ is the same or different from each other in each occurrence, and is selected from the group consisting of H, D, an aliphatic alkane having 1 to 10 carbons atoms, an aromatic hydrocarbon, and a substituted or unsubstituted aromatic ring or a heteroaromatic group having 5 to 10 carbon atoms;

Each of $Ar^1$-$Ar^3$ is the same or different from each other in each occurrence, and is an unsubstituted or a $R^1$-substituted aromatic hydrocarbon or heteroaromatic cylic hydrocarbon system;

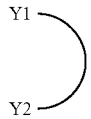

is a bidentate ligand.

M is a transitional metal.

m is any one of numbers 0-3, and n is any one of numbers 1-3.

In one preferred embodiment, the organic metal complex of present disclosure is selected from the following general formulas:

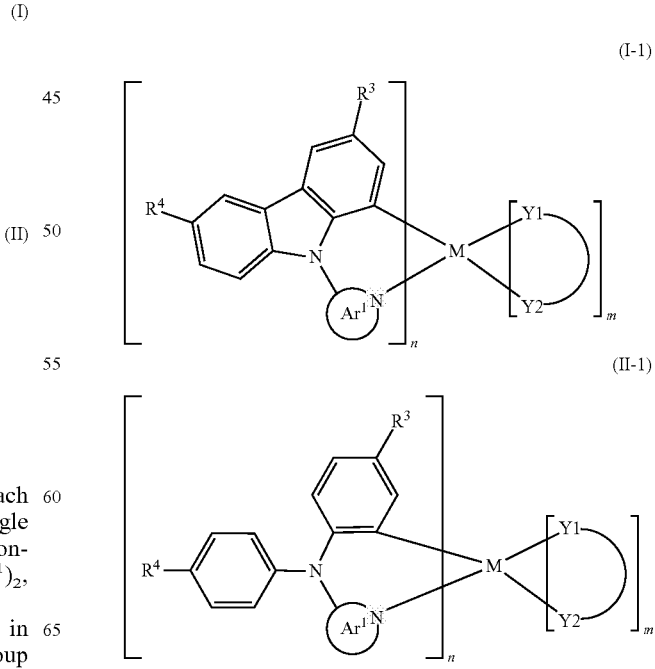

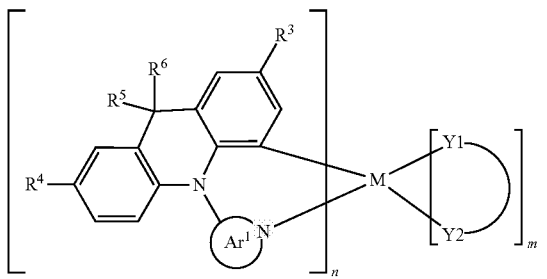 (I-2)

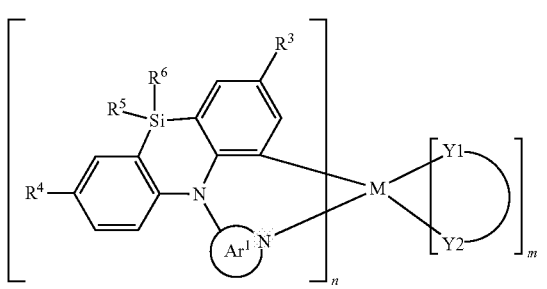 (I-3)

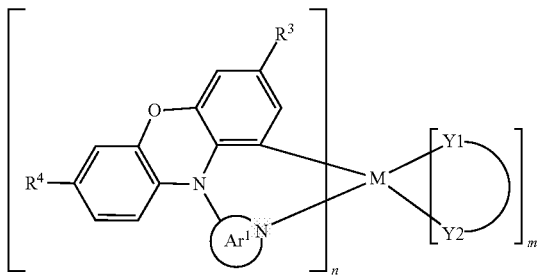 (I-4)

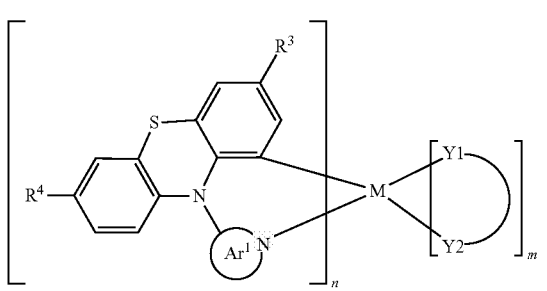 (I-5)

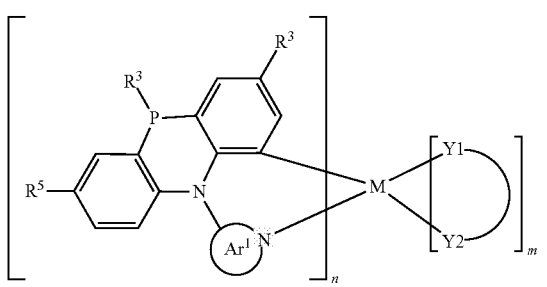 (I-6)

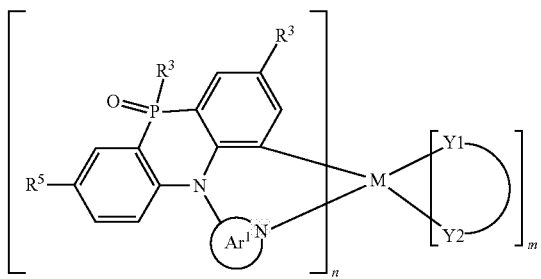 (I-7)

wherein each of $R^3$, $R^4$, $R^5$ and $R^6$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane, or cycloalkane containing 1 to 10 carbon atoms; alkane ether or alkane thioether group containing 3 to 10 carbon atoms; and aryl group containing 6 to 10 carbon atoms.

Wherein,

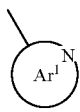

is N-hetero-six-membered ring unit, and is independently selected from general formulas C1 to C4 in multiple occurrences:

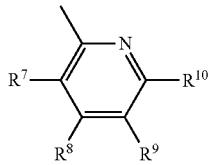 C1

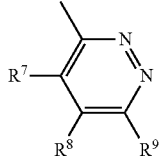 C2

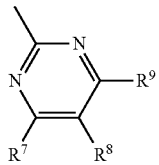 C3

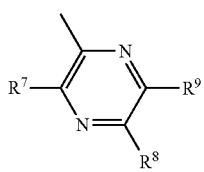 C4

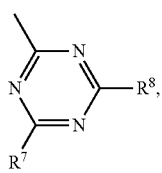
C5

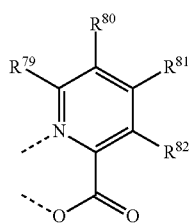
L4

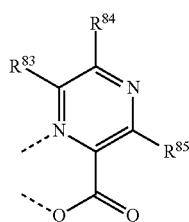
L5 wherein each of $R^1$ to $R^9$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane or cycloalkane containing 1 to 10 carbon atoms; alkane ether or alkane thioether group containing 3 to 10 carbon atoms, and aryl group containing 6 to 10 carbon atoms.

Wherein

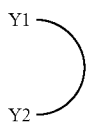

is a single anion ligand.

In some preferred embodiments, the single anion ligand is independently selected from the following general formulas L1 to L15 in multiple occurrences:

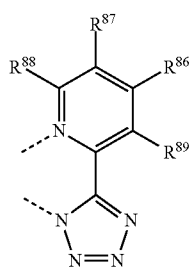
L6

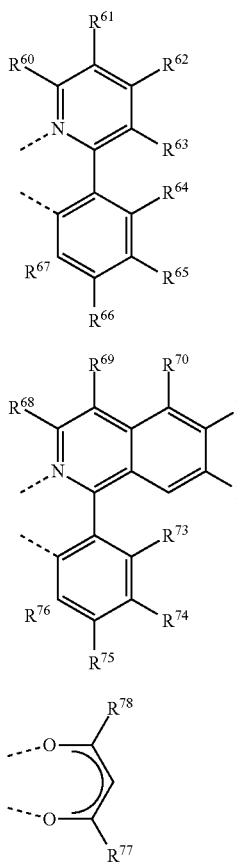

L1

L2

L3

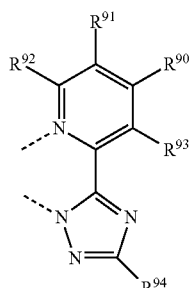
L7

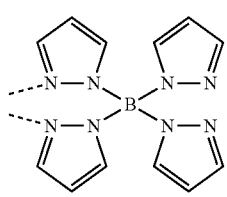
L8

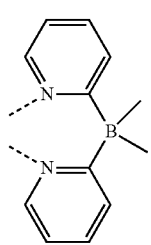
L9

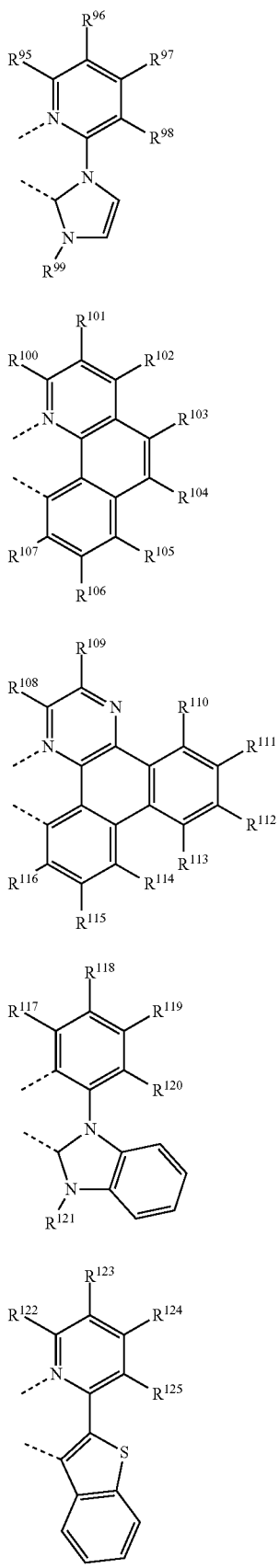

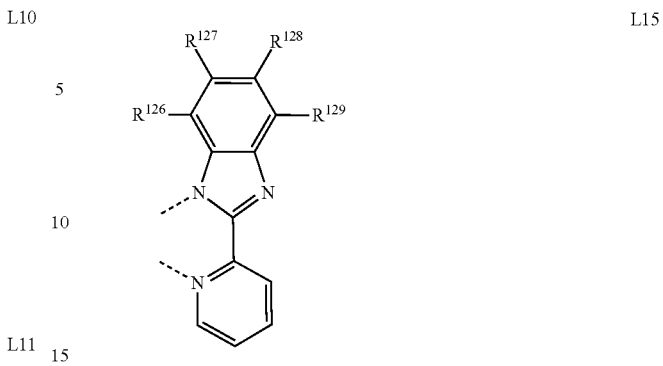

wherein each of $R^{60}$ to $R^{129}$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane or cycloalkane containing 1 to 10 carbon atoms; alkane ether or alkane thioether group containing 3 to 10 carbon atoms, and aryl group containing 6 to 10 carbon atoms, wherein the dashed line indicates connecting with the metal element M in the form of a single bond.

In the organic metal complex of the present disclosure, M is a transition metal element.

In one preferred embodiment, M is any one selected from the group consisting of Cr, Mo, W, Ru, Rh, Ni, Ag, Cu, Zn, Pd, Au, Os, Re, Ir and Pt. In one particularly preferred embodiment, M is selected from Ir or Pt.

From the viewpoint of the heavy atom effect, Ir or Pt is preferably used as the central metal M of the above-mentioned metal organic complex. Iridium is particularly preferred, since iridium is chemically stable and has a significant heavy atom effect that results in high luminous efficiency.

Specific examples of suitable metal organic complexes according to the present disclosure are given below, but the present disclosure is not limited to these metal complexes:

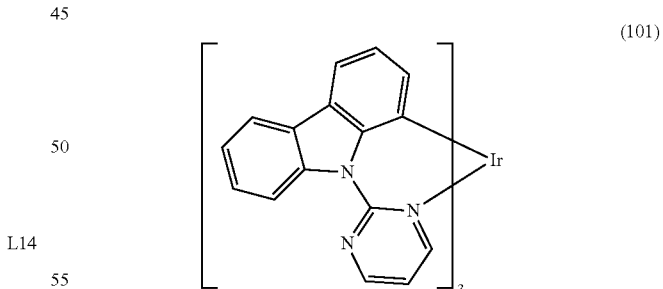

(101)

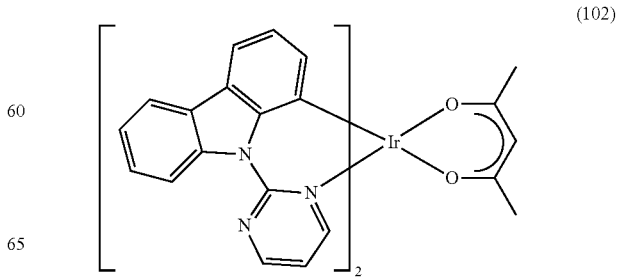

(102)

-continued
(103)
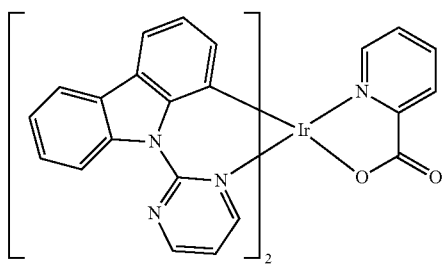
(104)
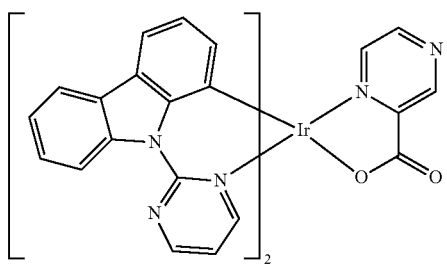
(105)
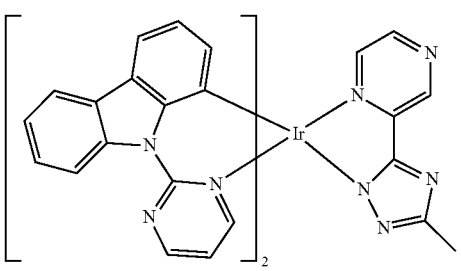
(106)
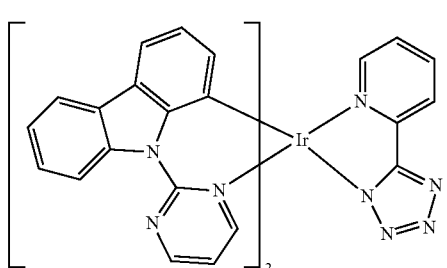
(107)
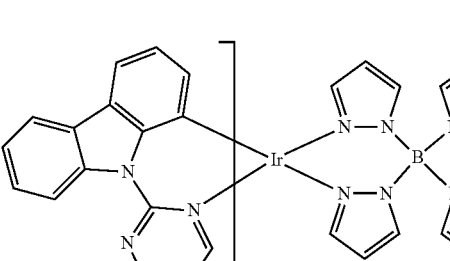
(108)
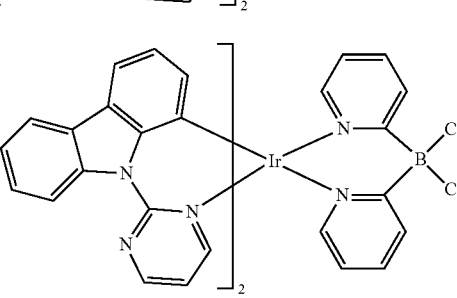
-continued
(109)
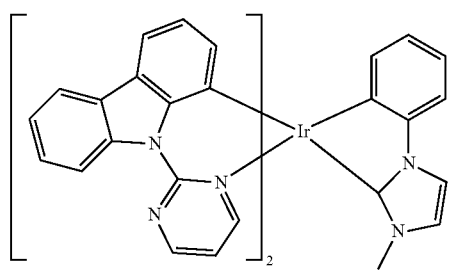
(110)
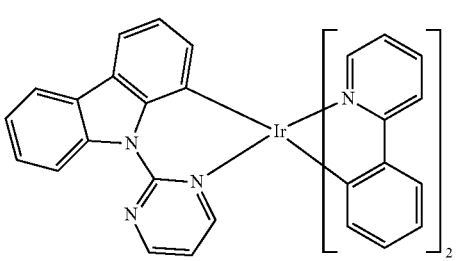
(111)
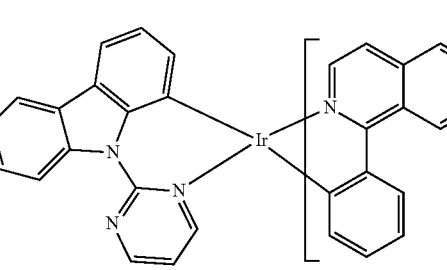
(112)
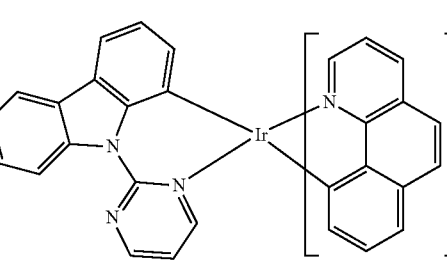
(113)
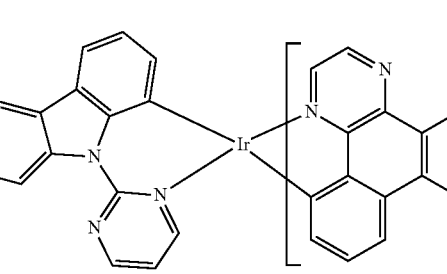
(114)
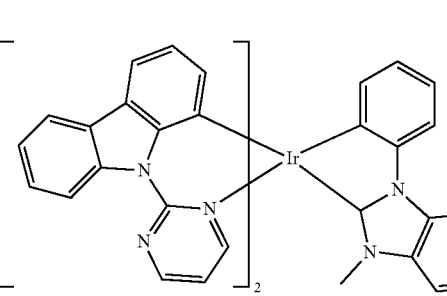

(115) 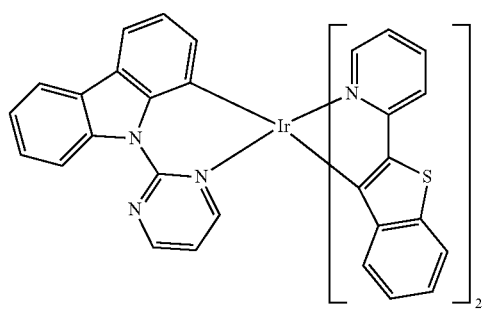
(116) 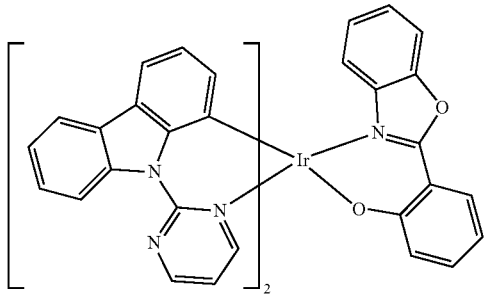
(117) 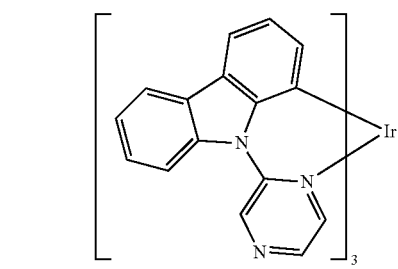
(118) 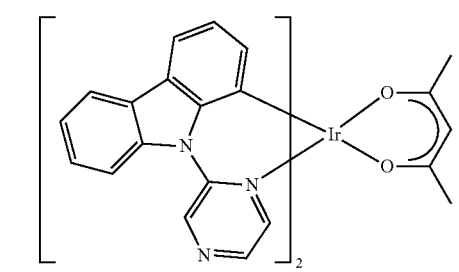
(119) 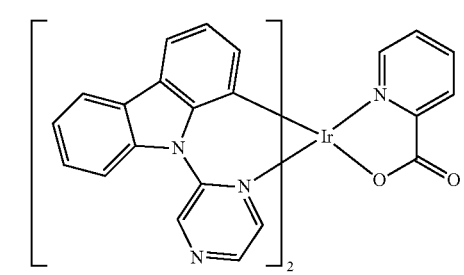
(120) 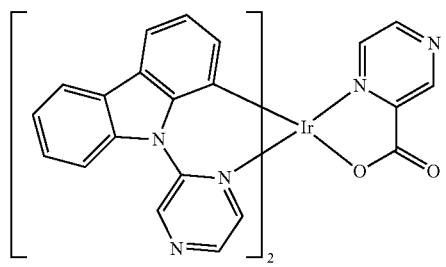
(121) 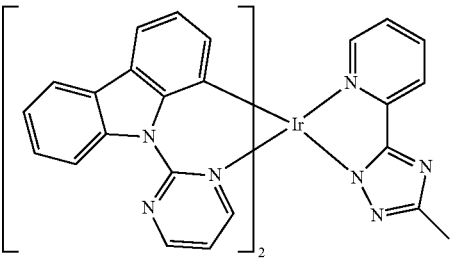
(122) 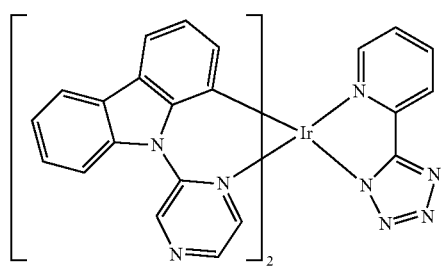
(123) 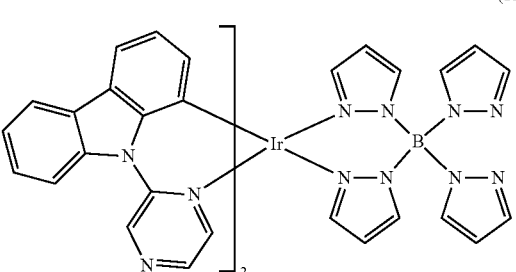
(124) 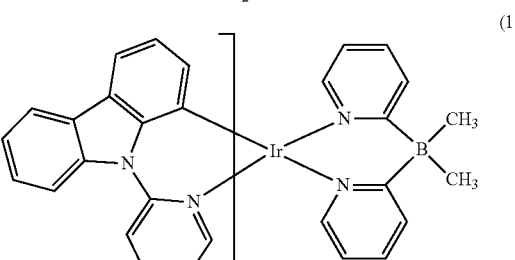
(125) 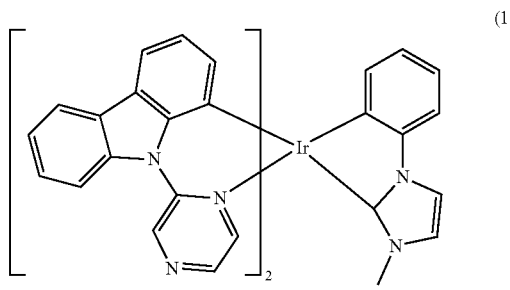

-continued
(126)
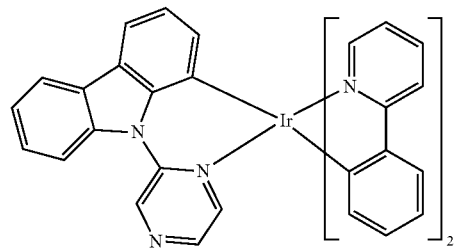
(127)
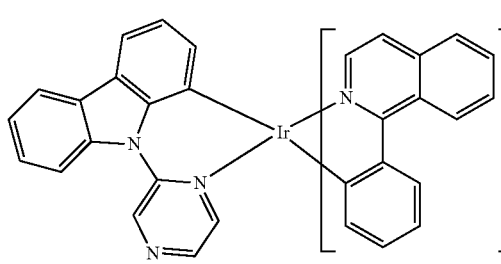
(128)
(129)
(130)
-continued
(131)
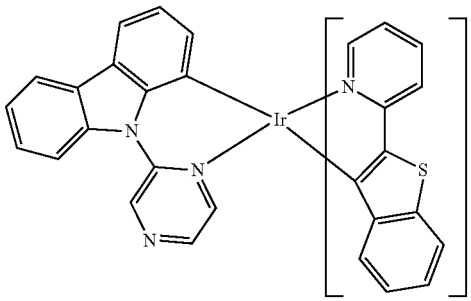
(132)
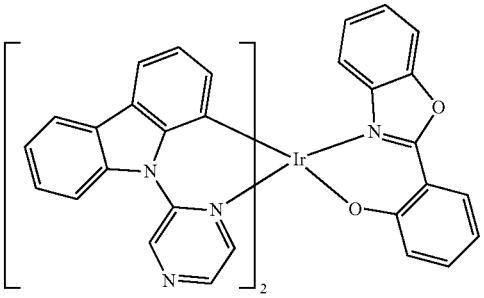
(133)
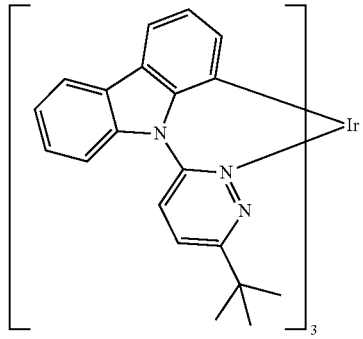
(134)
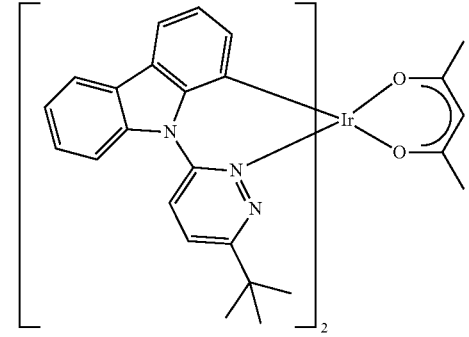
(135)
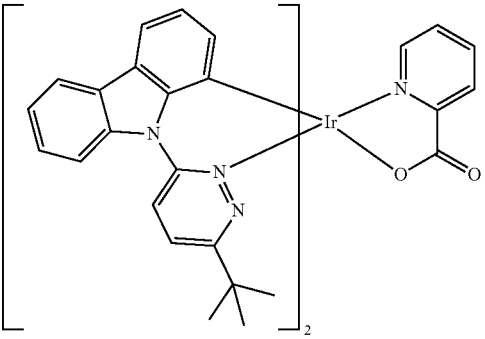

(136) 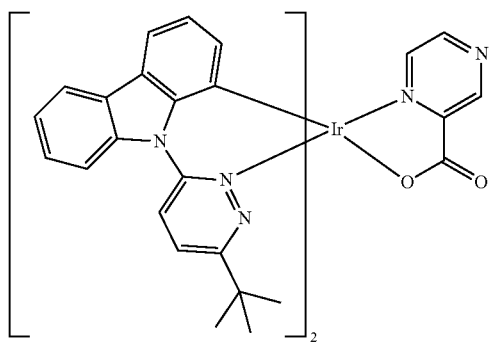
(137) 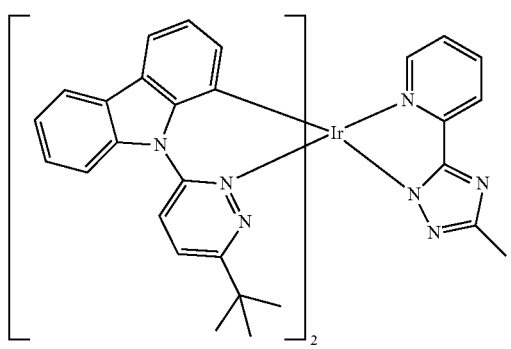
(138) 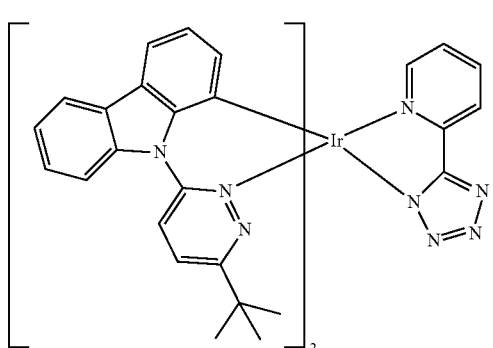
(139) 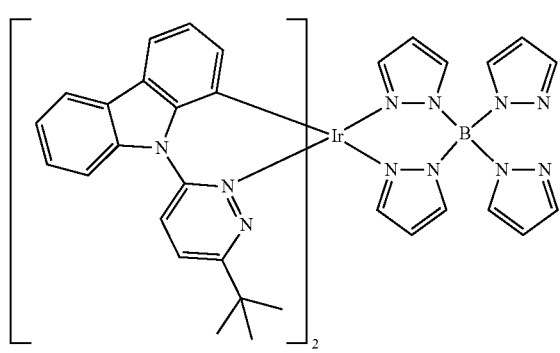
(140) 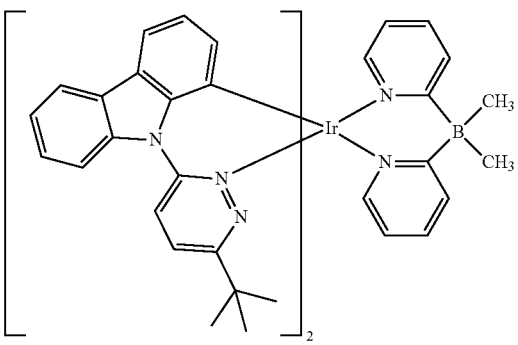
(141) 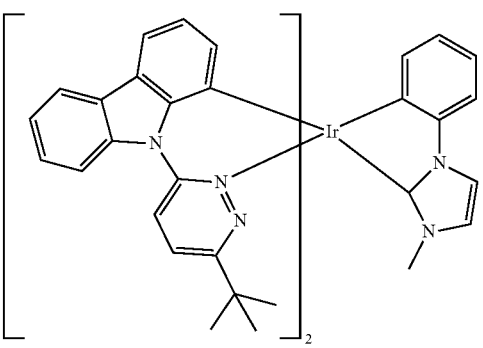
(142) 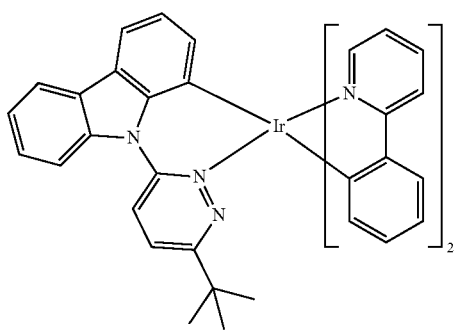
(143) 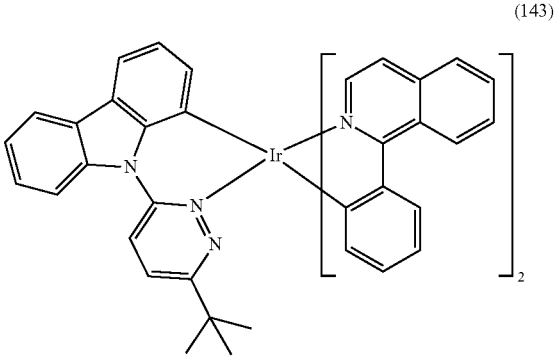

(144) 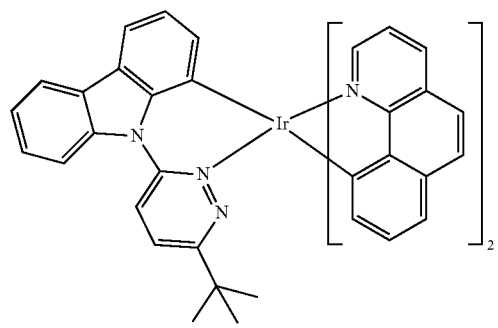
(145) 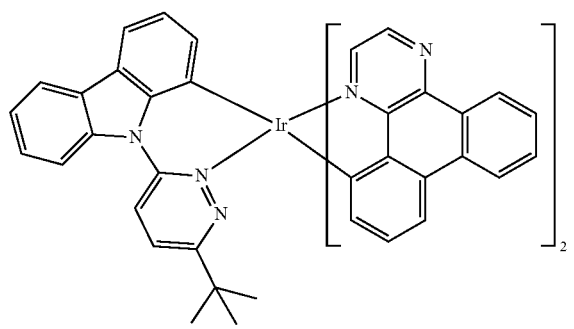
(146) 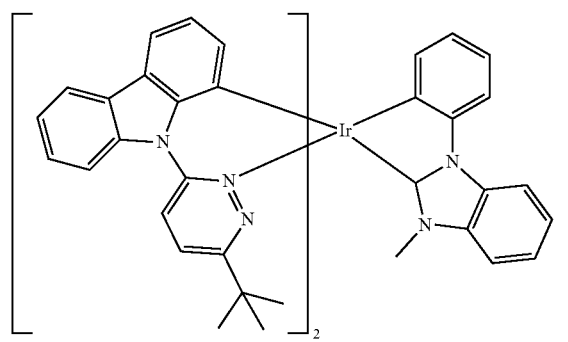
(147) 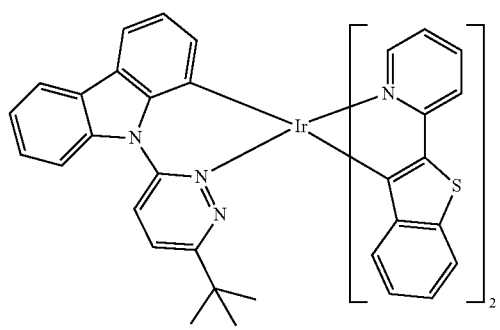
(148) 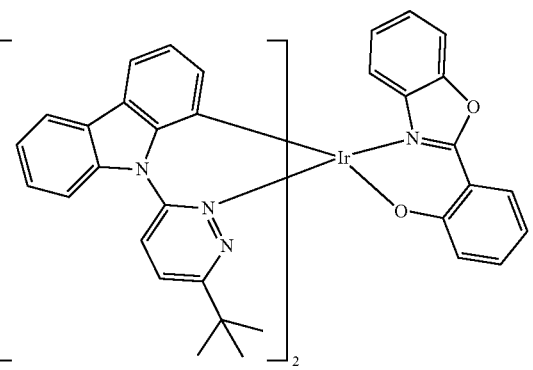
(149) 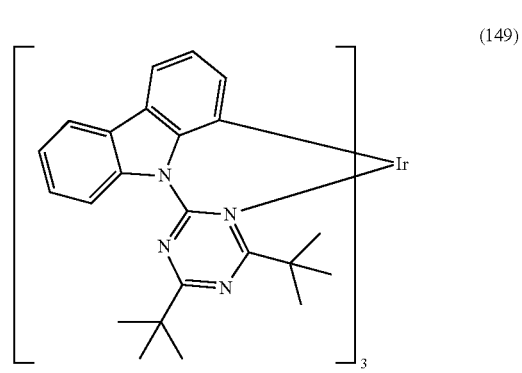
(150) 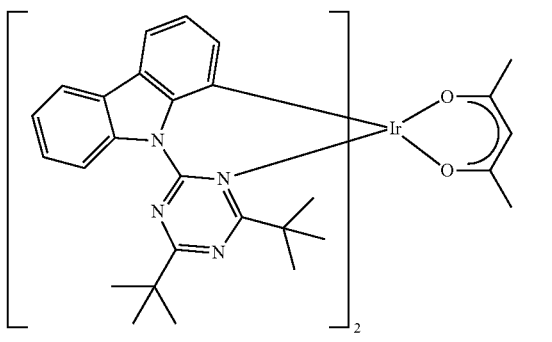
(151) 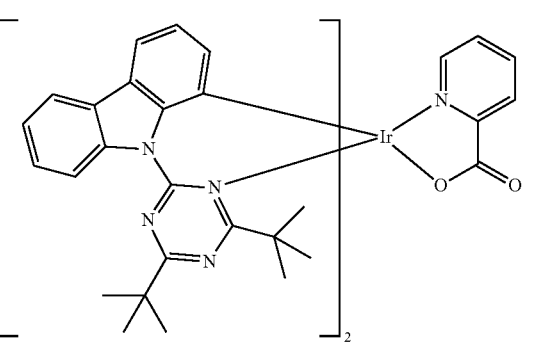

-continued
(152)
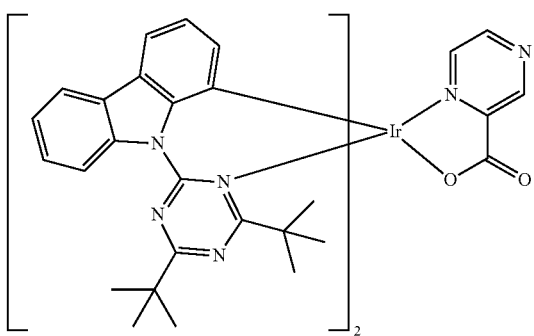
(153)
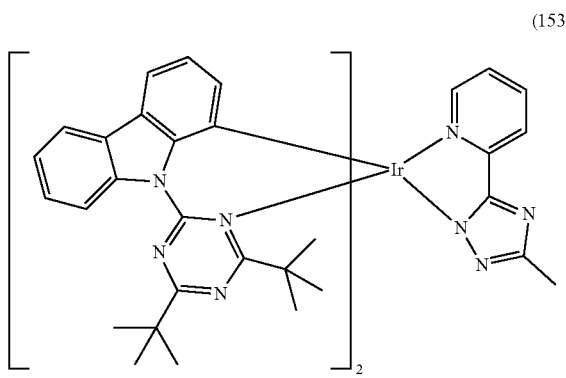
(154)
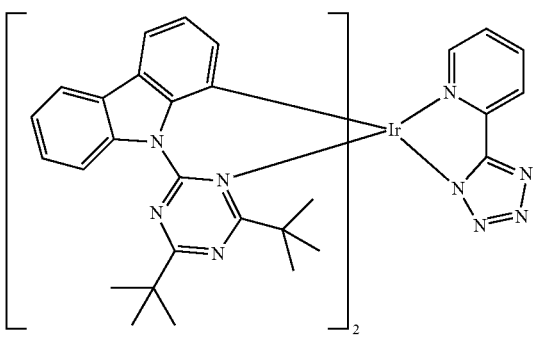
(155)
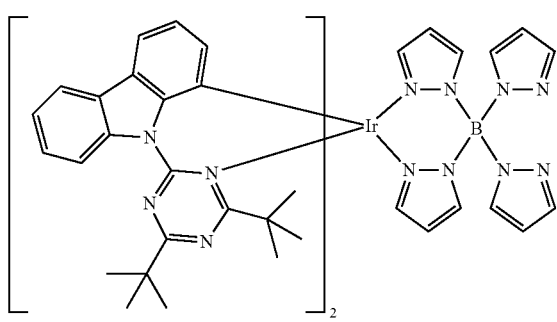
-continued
(156)
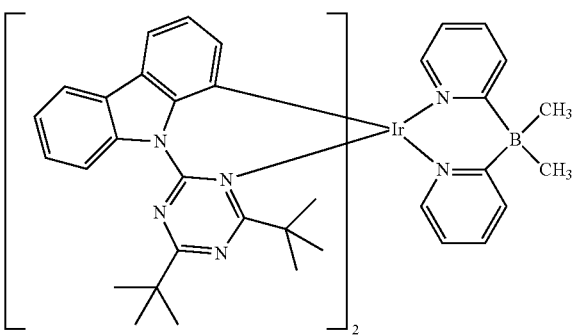
(157)
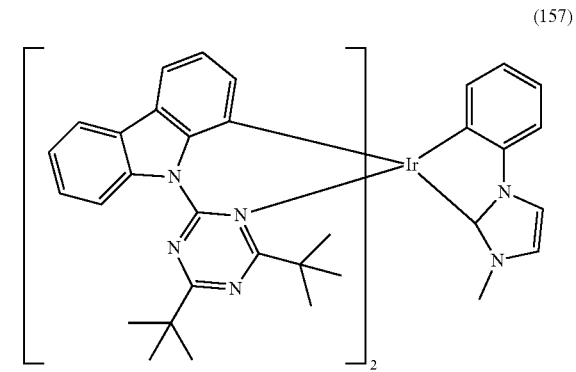
(158)
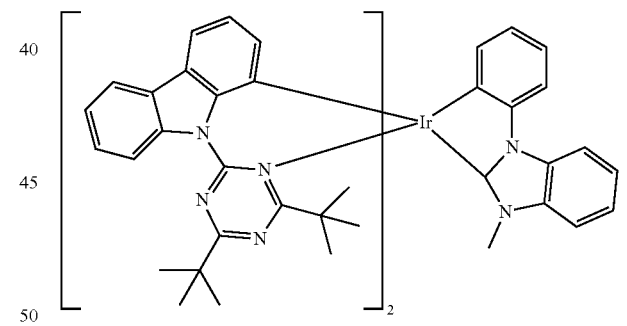
(159)
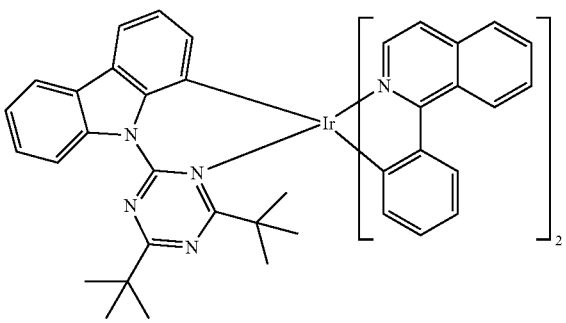

(160)
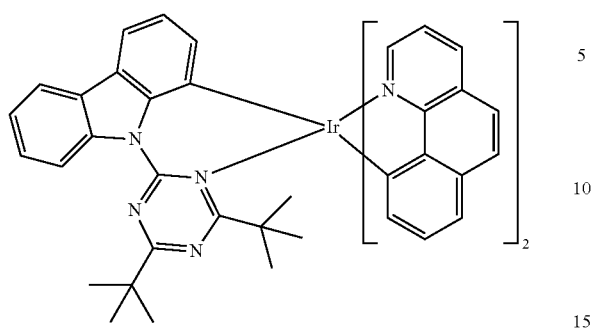
(161)
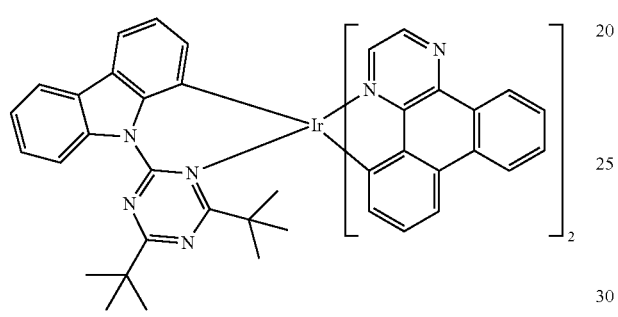
(162)
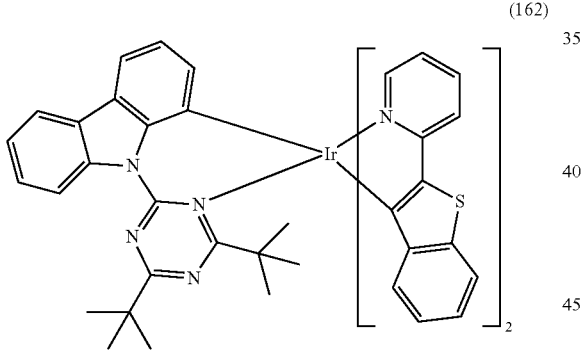
(163)
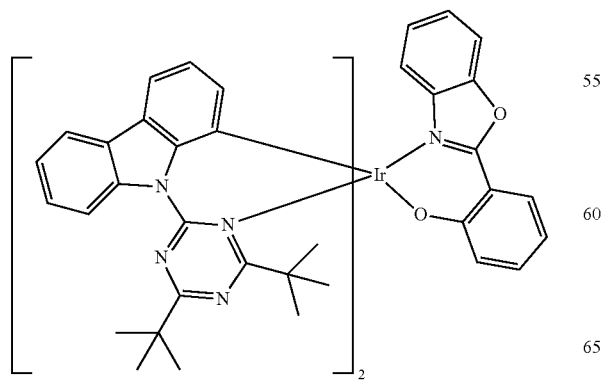
(164)
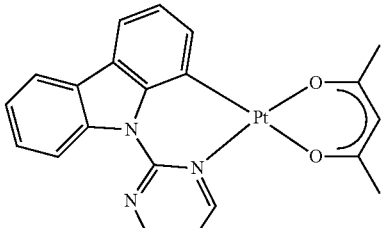
(165)
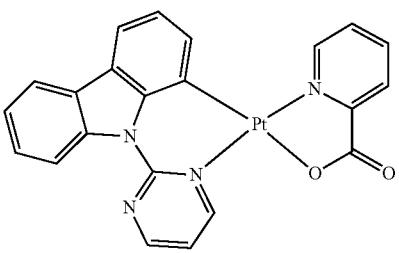
(166)
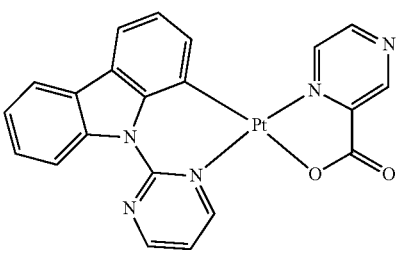
(167)
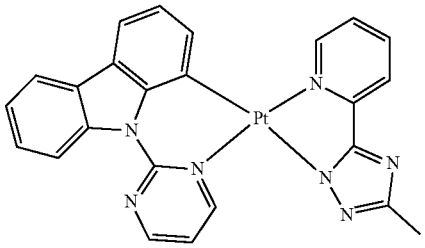
(168)
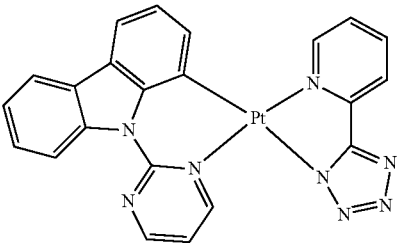
(169)
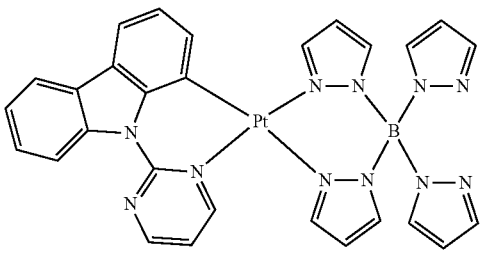

(170) 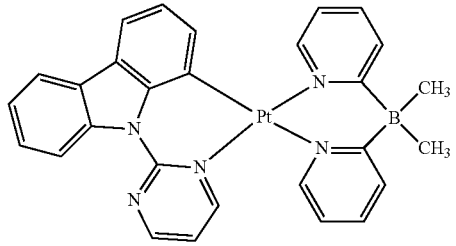
(171) 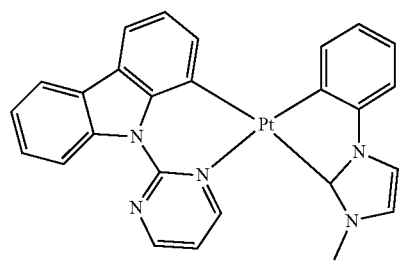
(172) 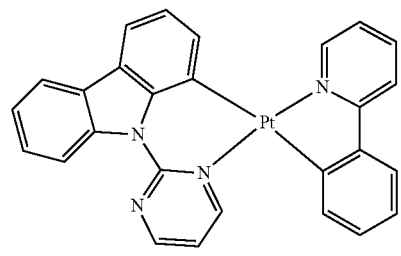
(173) 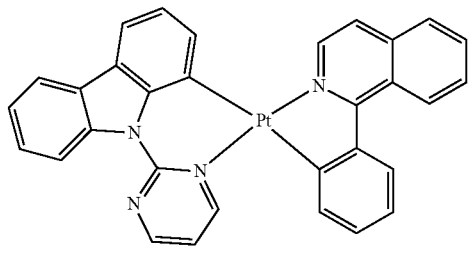
(174) 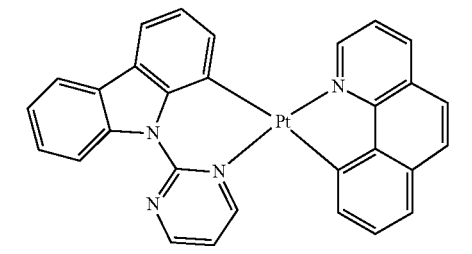
(175) 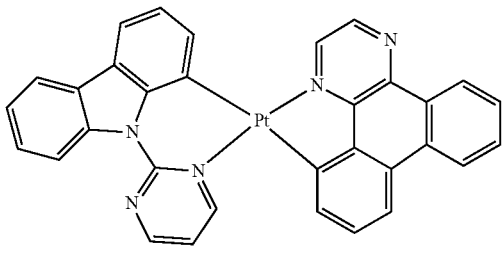
(176) 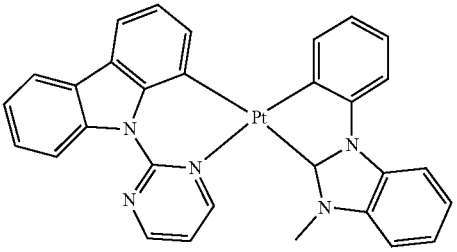
(177) 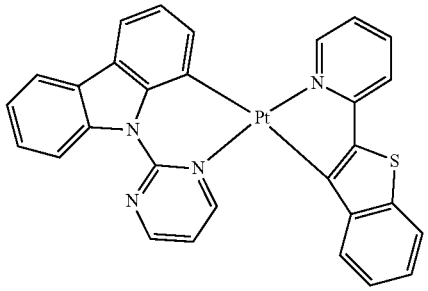
(178) 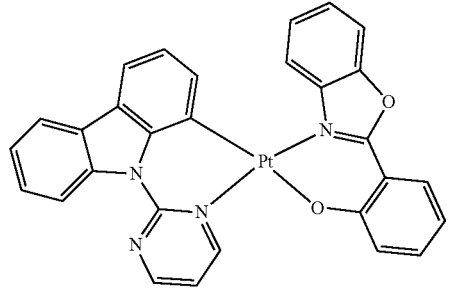
(179) 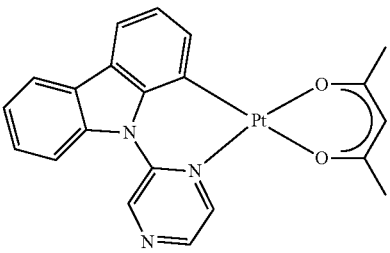
(180) 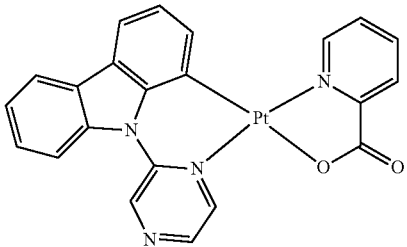
(181)

(182) 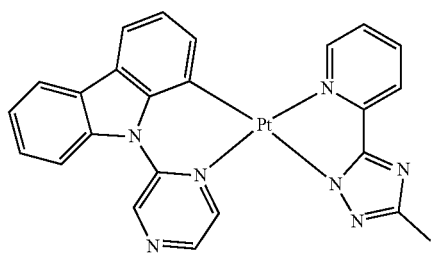

(183) 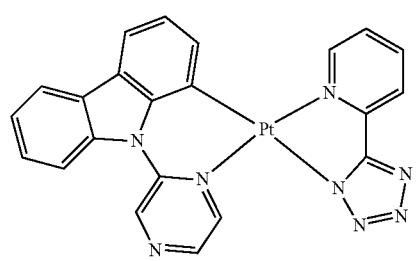

(184) 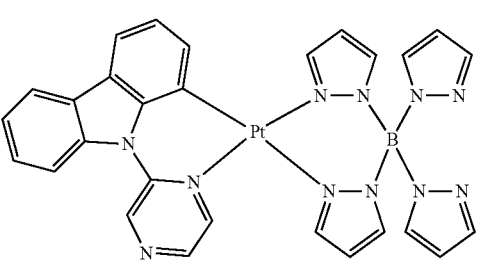

(185) 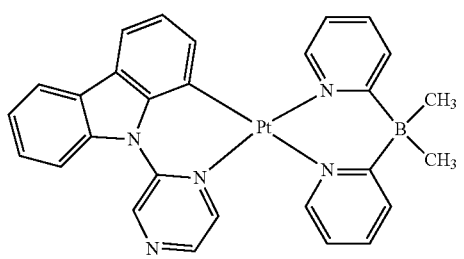

(186) 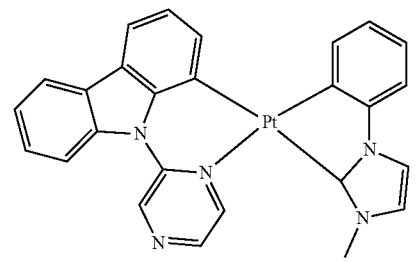

(187) 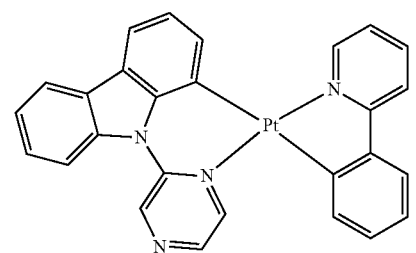

(188) 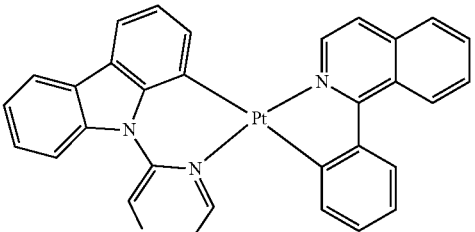

(189) 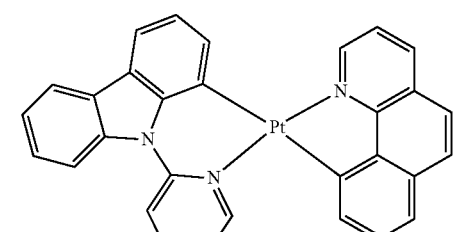

(190) 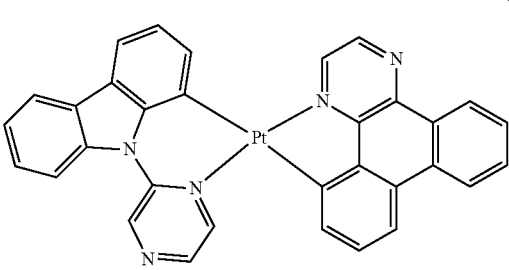

(191) 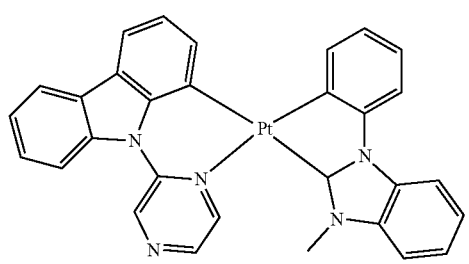

(192) 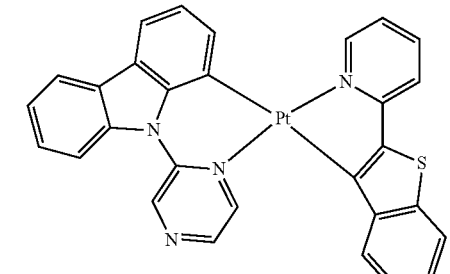

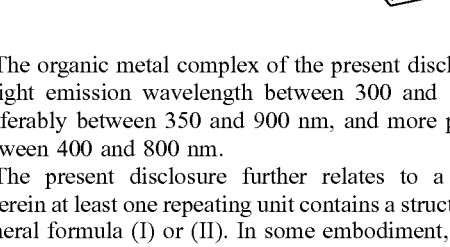

The organic metal complex of the present disclosure has a light emission wavelength between 300 and 1000 nm, preferably between 350 and 900 nm, and more preferably between 400 and 800 nm.

The present disclosure further relates to a polymer, wherein at least one repeating unit contains a structure of the general formula (I) or (II). In some embodiment, the polymer may be non-conjugated polymers in which the structure unit represented by the general formula (I) or (II) is on the side chain. In another preferred embodiment, the polymer is conjugated polymers.

The present disclosure further relates to a mixture comprising the organic metal complex or the mixture of the present disclosure, and at least one of the other organic functional materials.

The other organic functional materials includes hole (also referred to as electron hole) injecting or transport material (HIM/HTM), hole-blocking material (HBM), electron-injection or transport material (EIM/ETM), electron-blocking material (EBM), organic host material (Host), singlet emitter (fluorescent emitter), multiplet emitter (phosphorescent emitter), especially light-emitting organic metal complexes. Non-limiting examples of various organic functional materials are described, for example, in WO2010135519A1, US20090134784A1, and WO 2011110277A1, whole contents of which are incorporated herewith by reference.

The organic functional material may be a small-molecule polymeric material.

As used herein, the term "small molecule" refers to a molecule that is not a polymer, an oligomer, a dendrimer, or a blend. In particular, there is no repetitive structure in small molecules. The molecular weight of the small molecule is no greater than 3000 g/mole, more preferably no greater than 2000 g/mole, and most preferably no greater than 1500 g/mole.

As used herein, the term "polymer" includes homopolymer, copolymer, and block copolymer. In addition, in the present disclosure, the polymer also includes dendrimer. The synthesis and application of dendrimers are described in Dendrimers and Dendrons, Wiley-VCH Verlag GmbH & Co. KGaA, 2002, Ed. George R. Newkome, Charles N. Moorefield, Fritz Vogtle.

The term "conjugated polymer" as defined herein is a polymer whose backbone is predominantly composed of the $sp^2$ hybrid orbital of carbon (C) atom. Some known non-limiting examples are: polyacetylene and poly (phenylene vinylene), on the backbone of which the C atom can also be optionally substituted by other non-C atoms, and which is still considered to be a conjugated polymer when the $sp^2$ hybridization on the backbone is interrupted by some natural defects. In addition, the conjugated polymer in the present disclosure may also comprise aromatic amine, aryl phosphine and other heteroarmotics, organic metal complexes, and the like.

In the present disclosure, the host material, the matrix material, Host material and Matrix material have the same meaning and are interchangeable.

In the present disclosure, the metal organic complex and the organic metal complex have the same meaning and are interchangeable.

The organic functional material is described in detail in the following (but not limited thereto).

1. HIM/HTM/EBM

Suitable organic HIM/HTM materials may include any one of the compounds having the following structural units: phthalocyanines, porphyrins, amines, aromatic amines, biphenyl triaromatic amines, thiophenes, thiophenes such as dithiophenethiophene and thiophthene, pyrrole, aniline, carbazole, indeno-fluorene, and derivatives thereof. Other suitable HIMs also include: fluorocarbon-containing polymers; polymers containing conductive dopants; conductive polymers such as PEDOT/PSS; self-assembled monomers such as compounds containing phosphonic acid and silane derivatives; metal oxides, such as MoOx; metal complex, and a crosslinking compound, and the like.

The electron blocking layer (EBL) is typically used to block electrons from adjacent functional layers, particularly light emitting layers. In contrast to a light-emitting device without a blocking layer, the presence of EBL usually results in an increase in luminous efficiency. The electron blocking layer (EBL) of the electron blocking material (EBM) requires a higher LUMO than that of the adjacent functional layer, such as the light emitting layer. In a preferred embodiment, the EBM has a greater energy level of excited state than that of the adjacent light emitting layer, such as a singlet or triplet level, depending on the emitter. In another preferred embodiment, the EBM has a hole transport function. HIM/HTM materials, which typically have high LUMO levels, can be used as EBM.

Other examples of cyclic aromatic amine derivative compounds that may be used as HTM or HIM may include, but are not limited to, the general structure as follows:

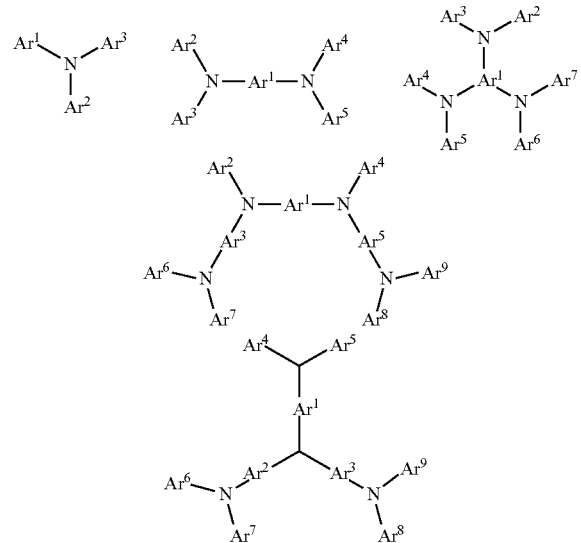

wherein each $Ar^1$ to $Ar^9$ may be independently selected from the group consisting of: cyclic aromatic hydrocarbon compounds such as benzene, biphenyl, triphenyl, benzo, naphthalene, anthracene, phenalene, phenanthrene, fluorene, pyrene, chrysene, perylene, azulene; and aromatic heterocyclic compounds such as dibenzothiophene, dibenzofuran, furan, thiophene, benzofuran, benzothiophene, benzoselenophene, carbazole, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, dibenzoselenophene, benzoselenophene, benzofuropyridine, indolocarbazole, pyridylindole, pyrrolodipyridine, furodipyridine, benzothienopyridine, thienodipyridine, benzoselenophenopyridine, and selenophenodipyridine; groups containing 2 to 10 membered ring structures which may be the same or different types of aromatic cyclic or aromatic heterocyclic groups and are bonded to each other directly or through at least one of the following groups, for example: oxygen atom, nitrogen atom, sulfur atom, silicon atom, phosphorus atom, boron atom, chain structure unit, and aliphatic cyclic group; and wherein each Ar may be further optionally substituted, and the substituents may optionally be hydrogen, alkyl, alkoxy, amino, alkene, alkyne, aralkyl, heteroalkyl, aryl and heteroaryl.

In one aspect, $Ar^1$ to $Ar^9$ may be independently selected from the groups of the group consisting of:

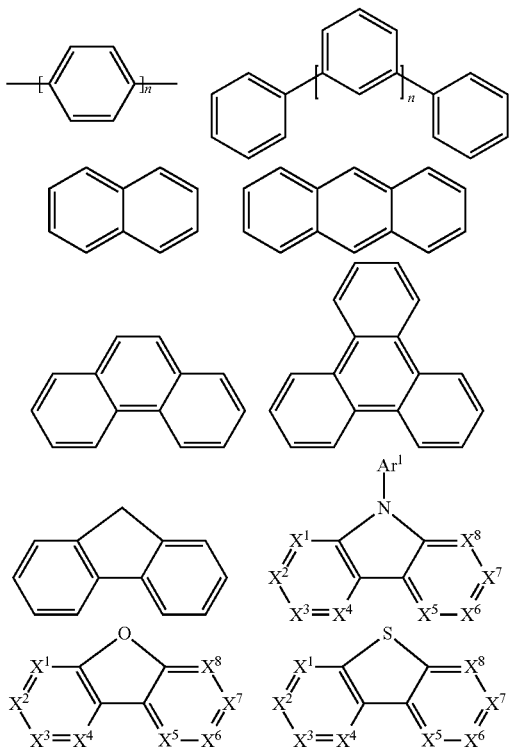

wherein n is an integer of 1 to 20; $X^1$ to $X^8$ are CH or N; Ar1 is as defined above.

Additional non-limiting examples of cyclic aromatic amine derivative compounds may be found in U.S. Pat. Nos. 3,567,450, 4,720,432, 3,615,404, and 5,061,569.

Examples of metal complexes that can be used as HTM or HIM include, but not limited to, the following general structures:

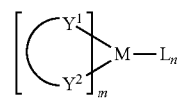

M is a metal, having an atomic weight greater than 40; $(Y^1-Y^2)$ is a bidentate ligand, wherein $Y^1$ and $Y^2$ are independently selected from the group consisting of C, N, O, P, and S; L is an auxiliary ligand; m is an integer from 1 to the maximum coordination number of the metal; m+n is the maximum coordination number of the metal.

In one embodiment, $(Y^1-Y^2)$ may be a 2-phenylpyridine derivative.

In another embodiment, $(Y^1—Y^2)$ may be a carbene ligand.

In another embodiment, M may be selected from the group consisting of Ir, Pt, Os, and Zn.

In another aspect, the HOMO of the metal complex that can be used as HTM or HIM is greater than −5.5 eV (relative to the vacuum level).

Examples of a suitable HIM/HTM/EBM compound are listed below

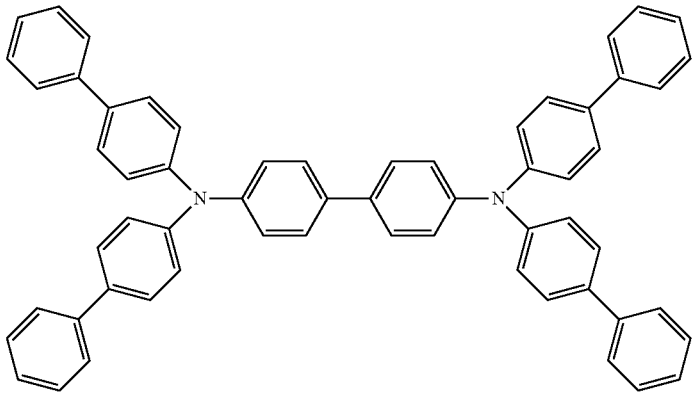

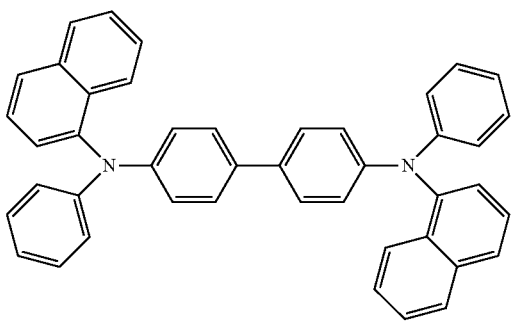

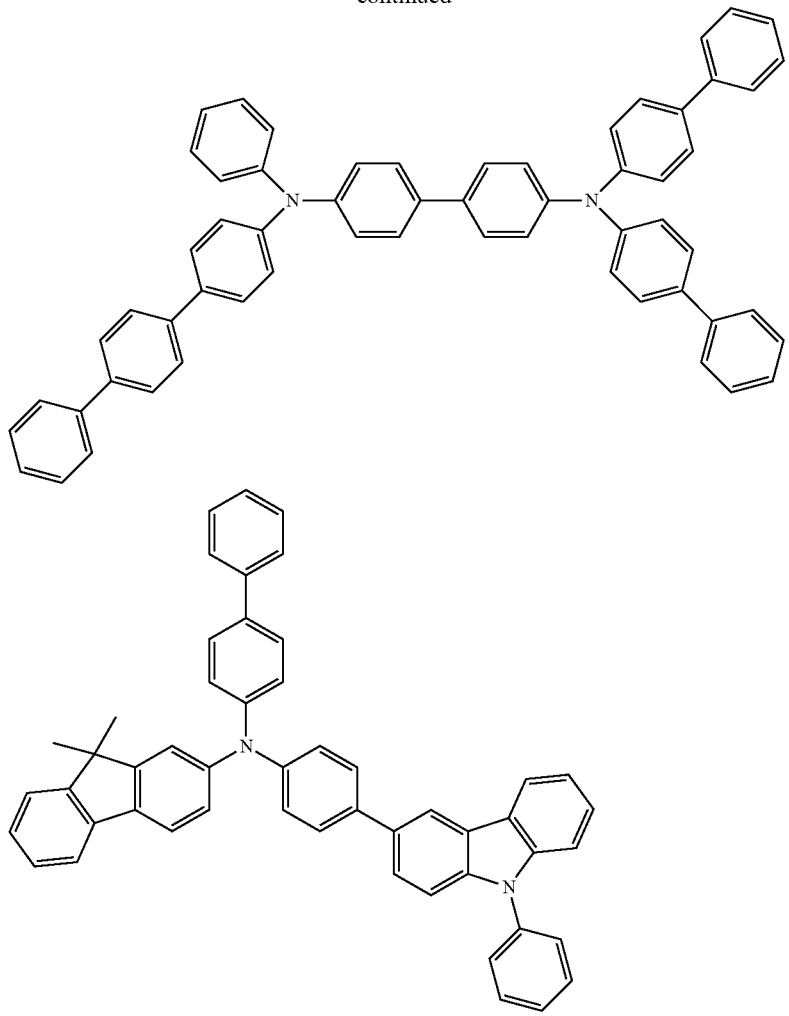

2. EIM/ETM/HBM

Examples of EIM/ETM material are not particularly limited, and any metal complex or organic compound may be used as EIM/ETM as long as they can transfer electrons. Preferred organic EIM/ETM materials may be selected from the group consisting of tris (8-quinolinolato) aluminum (AlQ3), phenazine, phenanthroline, anthracene, phenanthrene, fluorene, bifluorene, spiro-bifluorene, phenylene-vinylene, triazine, triazole, imidazole, pyrene, perylene, trans-indenofluorene, cis-indenonfluorene, dibenzol-indenofluorene, indenonaphthalene, benzanthracene and their derivatives.

The hole-blocking layer (HBL) is typically used to block holes from adjacent functional layers, particularly light-emitting layers. In contrast to a light-emitting device without a blocking layer, the presence of HBL usually leads to an increase in luminous efficiency. The hole-blocking material (HBM) of the hole-blocking layer (HBL) requires a lower HOMO than that of the adjacent functional layer, such as the light-emitting layer. In a preferred embodiment, the HBM has a greater energy level of excited state than that of the adjacent light-emitting layer, such as a singlet or triplet, depending on the emitter. In another preferred embodiment, the HBM has an electron-transport function. Typically, EIM/ETM materials with deep HOMO levels may be used as HBM.

In another aspect, compounds that may be used as EIM/ETM/HBM compounds may be molecules comprising at least one of the following groups:

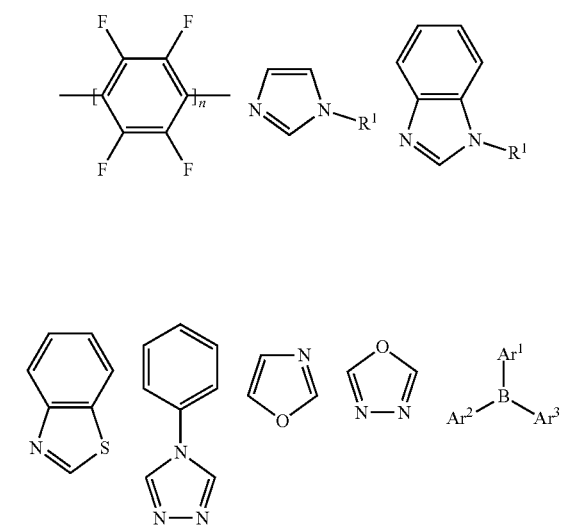

-continued

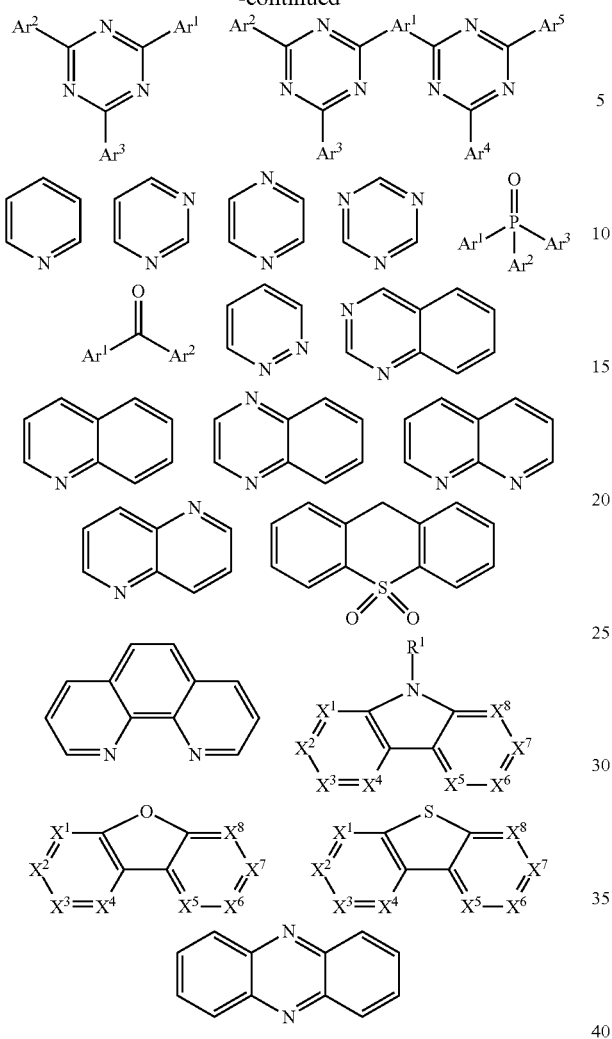

wherein R¹ may be selected from the group consisting of: hydrogen, alkyl, alkoxy, amino, alkene, alkyne, aralkyl, heteroalkyl, aryl and heteroaryl, wherein, when they are aryl or heteroaryl, they may have the same meaning as Ar¹ and Ar² in HTM as described above; Ar¹-Ar⁵ may have the same meaning as Ar¹ in HTM as described above; n is an integer from 0 to 20; and X¹-X⁸ may be selected from CR¹ or N.

On the other hand, examples of metal complexes that may be used as EIM/ETM may include, but are not limited to, the following general structure:

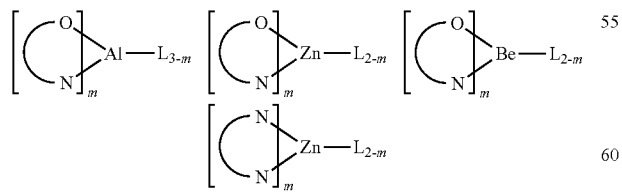

(O—N) or (N—N) is a bidentate ligand, wherein the metal coordinates with O, N, or N, N; L is an auxiliary ligand; and m is an integer whose value is from 1 to the maximum coordination number of the metal.

An example of a suitable ETM compound is listed below:

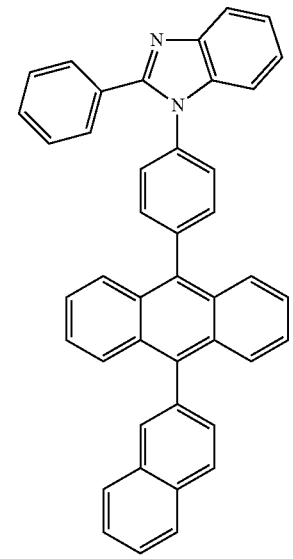

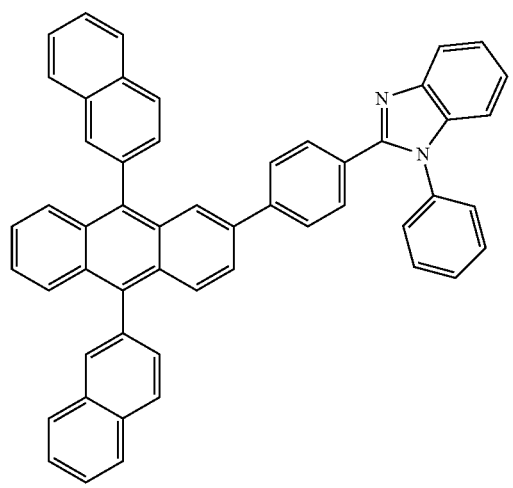

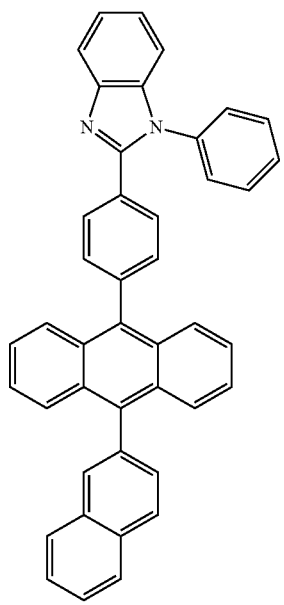

In another preferred embodiment, the organic alkali metal compound may be used as the EIM. In the present disclosure, the organic alkali metal compound may be understood as a compound having at least one alkali metal, i.e., lithium, sodium, potassium, rubidium, and cesium, and further comprising at least one organic ligand.

Suitable organic alkali metal compounds include the compounds described in U.S. Pat. No. 7,767,317 B2, EP 1941562B1 and EP 1144543B1.

The preferred organic alkali metal compound may be a compound of the following formula:

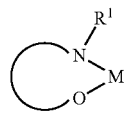

wherein $R^1$ has the same meaning as described above, and the arc represents two or three atoms and the bond to form a 5- or 6-membered ring with metal M when necessary, while the atoms may be optionally substituted by one or more $R^1$; and wherein M is an alkali metal selected from the group consisting of lithium, sodium, potassium, rubidium, and cesium.

The organic alkali metal compound may be in the form of a monomer, as described above, or in the form of an aggregate, for example, two alkali metal ions with two ligands, four alkali metal ions and four ligands, six alkali metal ions and six ligands, or in other forms.

The preferred organic alkali metal compound may be a compound of the following formula:

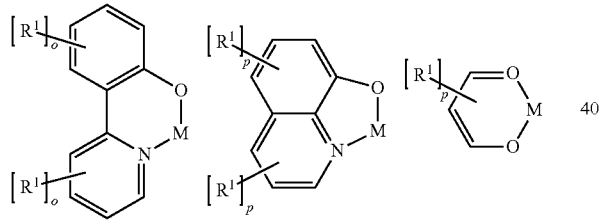

wherein, the symbols used are as defined above, and in addition:

o, it may be the same or different in each occurrence, selected from 0, 1, 2, 3 or 4; and p, it may be the same or different in each occurrence, selected from 0, 1, 2 or 3.

In a preferred embodiment, the alkali metal M is selected from the group consisting of lithium, sodium, potassium, more preferably lithium or sodium, and most preferably lithium.

In a preferred embodiment, the electron-injection layer includes the organic alkali metal compound, and more preferably the electron-injection layer consists of the organic alkali metal compound.

In another preferred embodiment, the organic alkali metal compound is doped into other ETMs to form an electron-transport layer or an electron-injection layer, more preferably an electron-transport layer.

Examples of a suitable organic alkali metal compound are listed below:

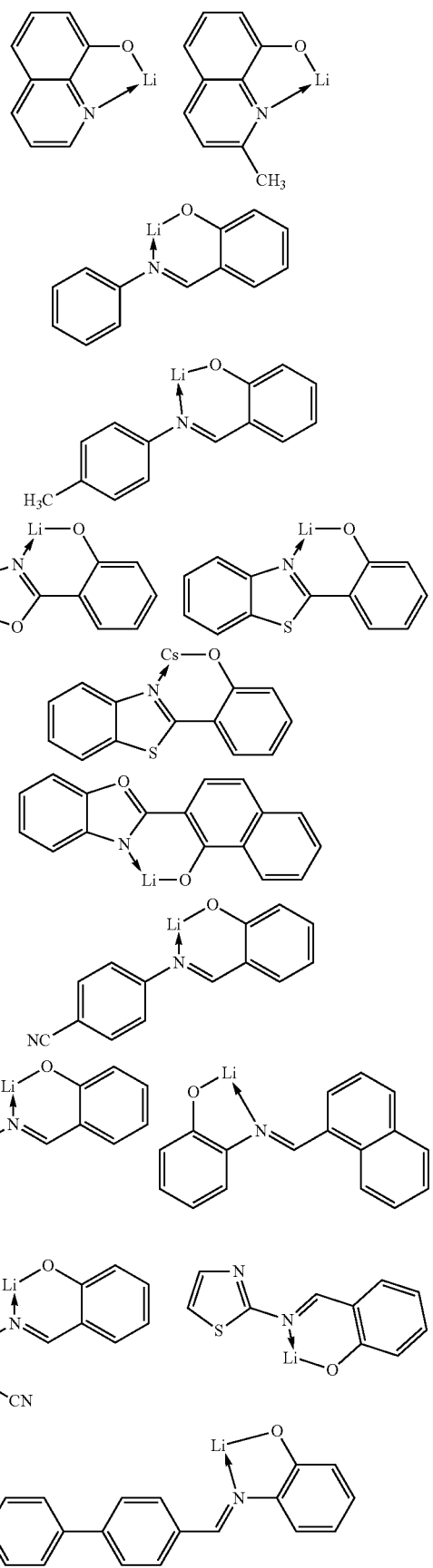

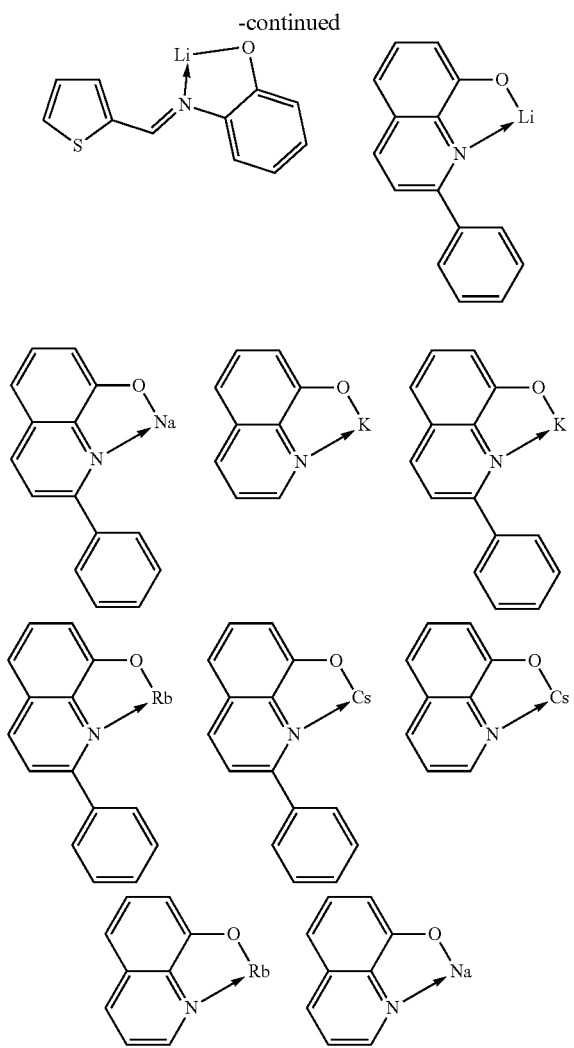

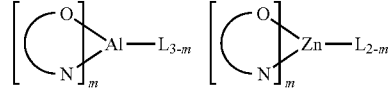

(O—N) is a bidentate ligand in which the metal is coordinated to O and N atoms.

In one embodiment, M may be selected from Ir and Pt.

Examples of organic compounds that may be used as triplet host are selected from the group consisting of: compounds containing cyclic aromatic hydrocarbon groups, such as benzene, biphenyl, triphenyl, benzo, and fluorene; compounds containing aromatic heterocyclic groups, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, or a combination thereof; groups containing 2 to 10 membered ring structures which may be the same or different types of aromatic cyclic or aromatic heterocyclic groups and are bonded to each other directly or through at least one of the following groups, for example: oxygen atom, nitrogen atom, sulfur atom, silicon atom, phosphorus atom, boron atom, chain structure unit, and aliphatic cyclic group; and wherein each Ar may be further optionally substituted, and the substituents may optionally be hydrogen, alkyl, alkoxy, amino, alkene, alkyne, aralkyl, heteroalkyl, aryl and heteroaryl.

In a preferred embodiment, the triplet host material may be selected from compounds comprising at least one of the following groups:

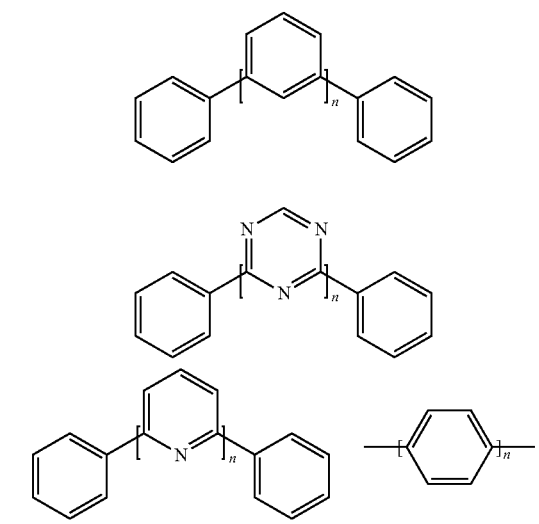

3. Triplet Host Materials

Examples of a triplet host material are not particularly limited and any metal complex or organic compound may be used as the host material as long as its triplet energy is greater than that of the emitter, especially a triplet emitter or phosphorescent emitter.

Examples of metal complexes that may be used as triplet hosts may include, but are not limited to, the general structure as follows:

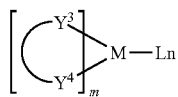

wherein M is a metal; $(Y^3-Y^4)$ may be a bidentate ligand, $Y^3$ and $Y^4$ may be independently selected from the group consisting of C, N, O, P, and S; L is an auxiliary ligand; m is an integer with the value from 1 to the maximum coordination number of the metal; and, m+n is the maximum number of coordination of the metal.

In a preferred embodiment, the metal complex which may be used as the triplet host has the following form:

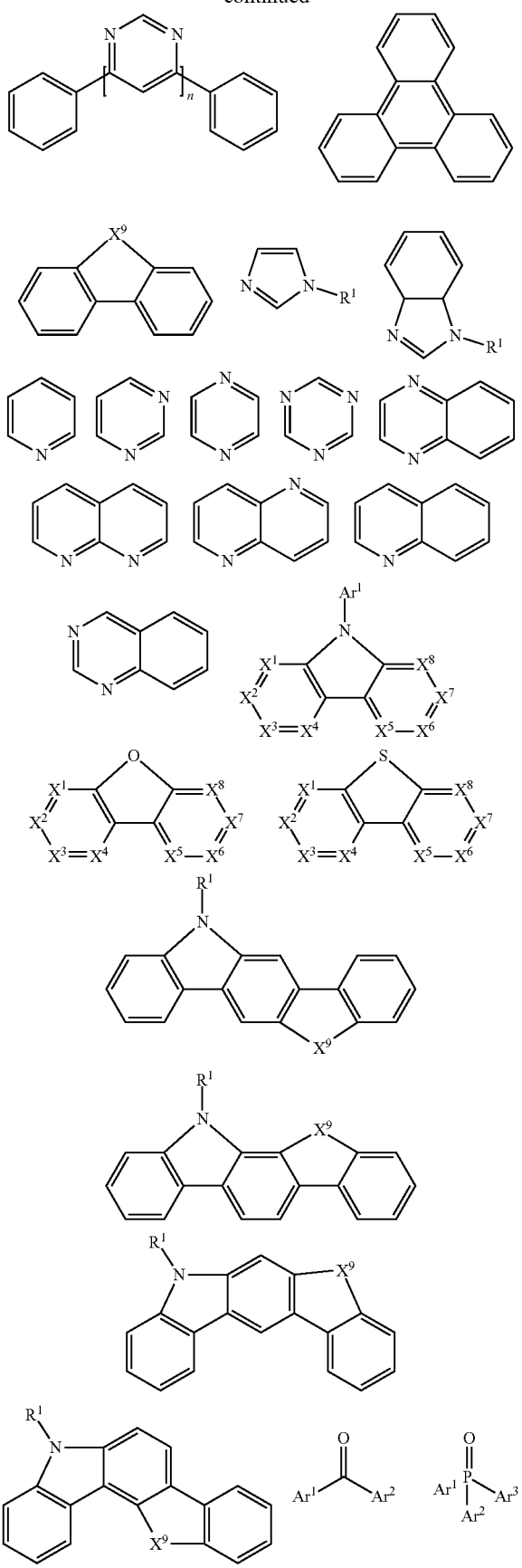

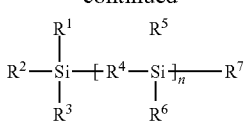

$R^1$-$R^7$ may be independently selected from the group consisting of hydrogen, alkyl, alkoxy, amino, alkene, alkyne, aralkyl, heteroalkyl, aryl and heteroaryl, which may have the same meaning as $Ar^1$ and $Ar^2$ described above when they are aryl or heteroaryl; n may be an integer from 0 to 20; $X^1$-$X^8$ may be selected from CH or N; and $X^9$ may be selected from $CR^1R2$ or NR1. $R^1$, $R^2$ have the same definition of $R^1$ in the ETM section.

Examples of suitable triplet host material are listed below:

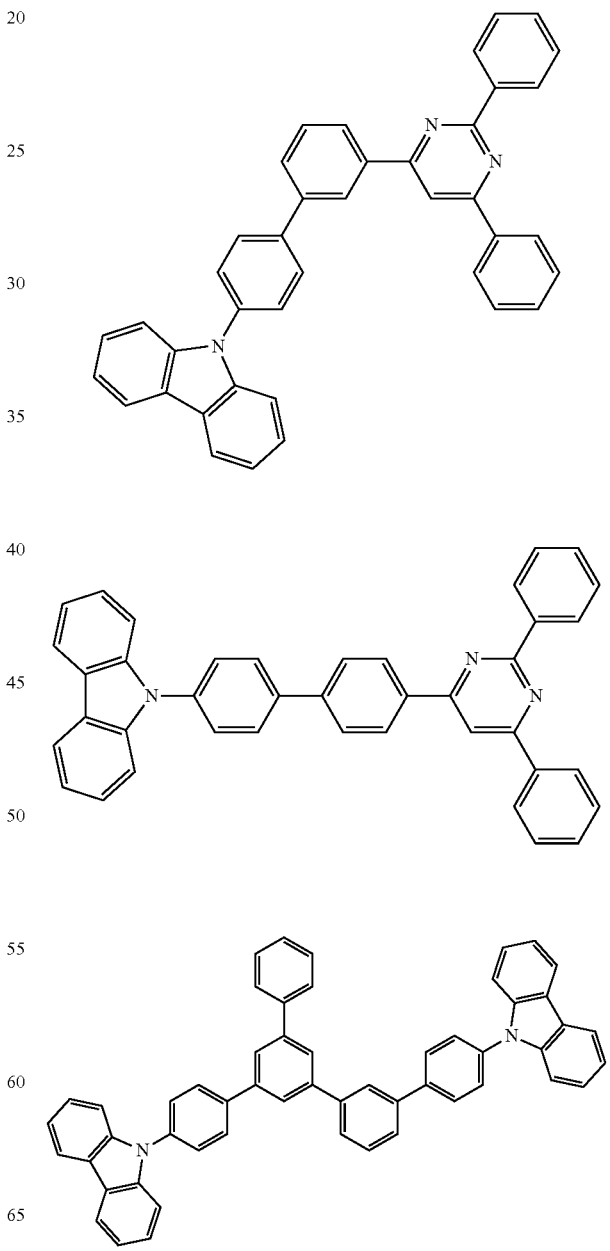

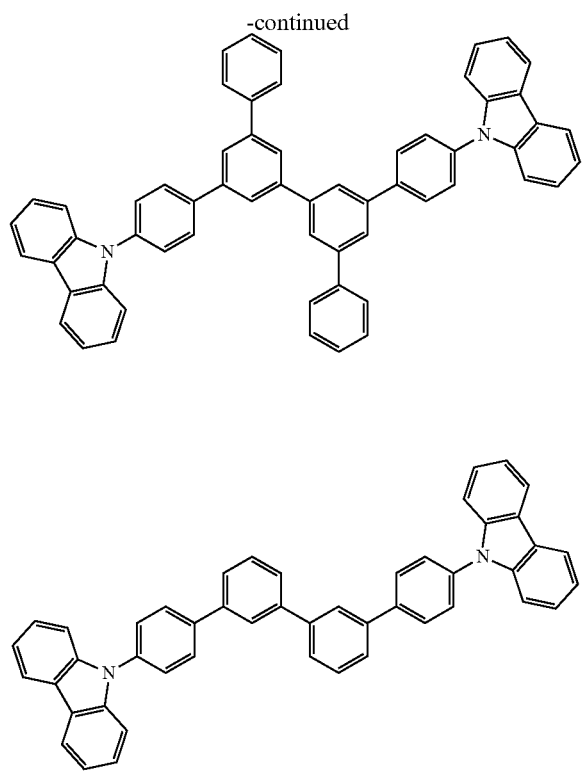

4. Singlet Host Material:

Examples of singlet host material are not particularly limited and any organic compound may be used as the host as long as its singlet state energy is greater than that of the emitter, especially the singlet emitter or fluorescent emitter.

Non-limiting examples of organic compounds used as singlet host materials may be selected from the group consisting of: compounds containing cyclic aromatic hydrocarbon groups, such as benzene, biphenyl, triphenyl, benzo, naphthalene, anthracene, phenalene, phenanthrene, fluorene, pyrene, chrysene, perylene, azulene; aromatic heterocyclic compounds, such as triphenylamine, dibenzothiophene, dibenzofuran, dibenzoselenophen, furan, thiophene, benzofuran, benzothiophene, benzoselenophene, carbazole, indolocarbazole, indolopyridine, pyrrolodipyridine, pyrazole, imidazole, triazole, isoxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indoxazine, bisbenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and groups comprising 2 to 10 membered ring structures, which may be the same or different types of aromatic cyclic or aromatic heterocyclic groups and are linked to each other directly or by at least one of the following groups, such as oxygen atom, nitrogen atom, sulfur atom, silicon atom, phosphorus atom, boron atom, chain structure unit, and aliphatic rings.

In a preferred embodiment, the singlet host material may be selected from compounds comprising at least one of the following groups:

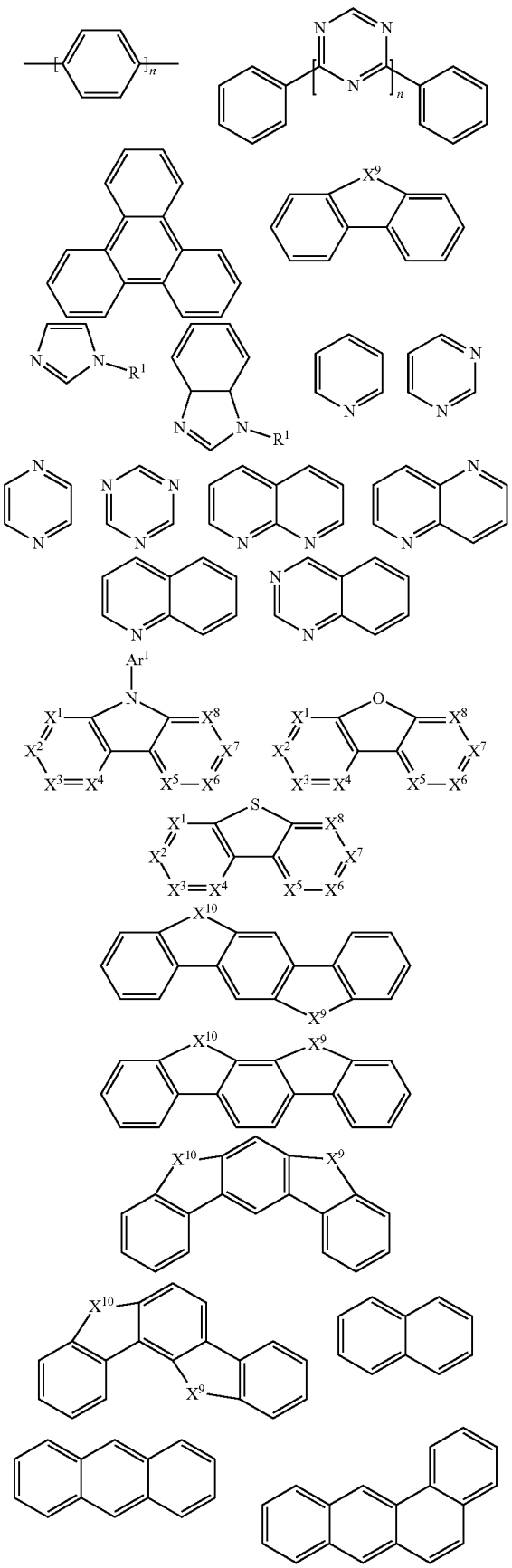

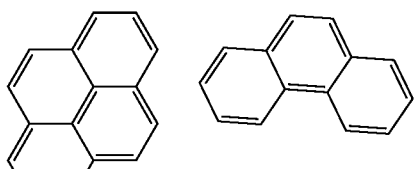

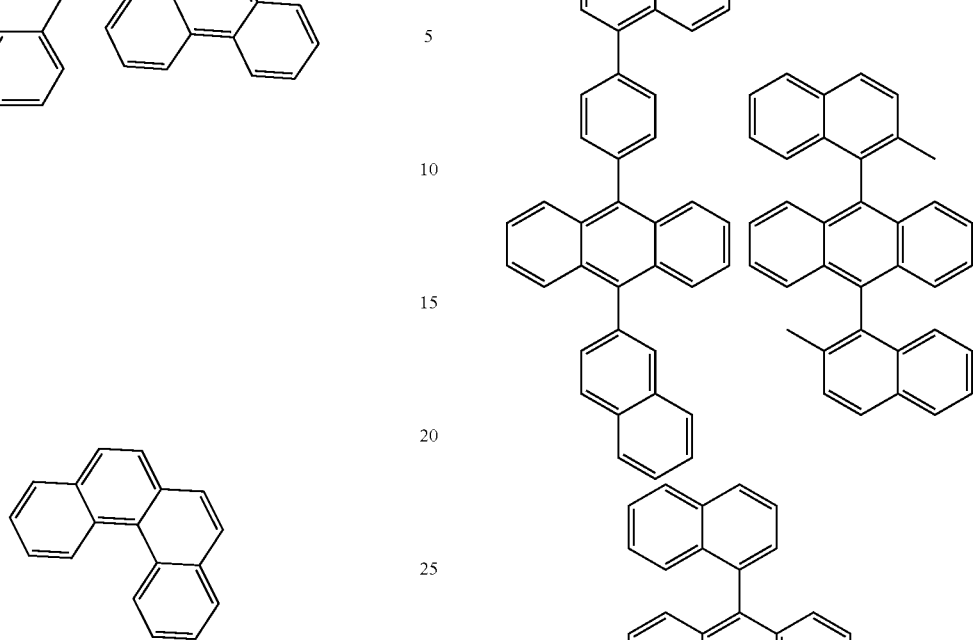

R[1] may be independently selected from the group consisting of hydrogen, alkyl, alkoxy, amino, alkene, alkyne, aralkyl, heteroalkyl, aryl and heteroaryl; Ar[1] is aryl or heteroaryl and has the same meaning as Ar[1] defined in the HTM above; n is an integer from 0 to 20; $X^1$-$X^8$ is selected from CH or N; $X^9$ and $X^{10}$ are selected from $CR^1R^2$ or $NR^1$.

Examples of a suitable singlet host material are listed below:

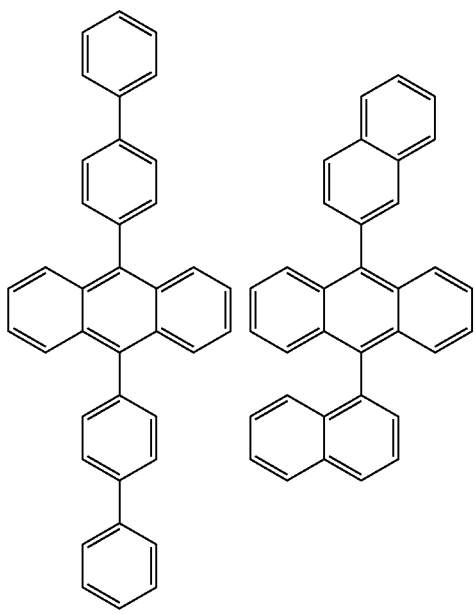

5. Singlet Emitter

The singlet emitter tends to have a longer conjugate π-electron system. To date, there have been many examples, such as, but not limited to, styrylamine and derivatives thereof disclosed in JP2913116B and WO2001021729A1, and indenofluorene and derivatives thereof disclosed in WO2008/006449 and WO2007/140847.

In a preferred embodiment, the singlet emitter may be selected from the group consisting of monostyrylamines, distyrylamines, tristyrylamines, tetrastyrylamines, styrylphosphines, styryl ethers, and arylamines.

Mono styrylamine refers to a compound which comprises an unsubstituted or optionally substituted styryl group and at least one amine, most preferably an aromatic amine. Distyrylamine refers to a compound comprising two unsubstituted or optionally substituted styryl groups and at least one amine, most preferably an aromatic amine. Ternarystyrylamine refers to a compound which comprises three unsubstituted or optionally substituted styryl groups and at least one amine, most preferably an aromatic amine. Quaternarystyrylamine refers to a compound comprising four unsubstituted or optionally substituted styryl groups and at least one amine, most preferably an aromatic amine. Preferred styrene is stilbene, which may be further optionally substituted. The corresponding phosphines and ethers are defined similarly to amines. Aryl amine or aromatic amine refers to a compound comprising three unsubstituted or optionally substituted aromatic cyclic or heterocyclic systems directly attached to nitrogen. At least one of these aromatic cyclic or heterocyclic systems is preferably selected from fused ring systems and most preferably has at least 14 aromatic ring atoms. Among the preferred examples are aromatic anthramine, aromatic anthradiamine, aromatic pyrene amines, aromatic pyrene diamines, aromatic chrysene amines and aromatic chrysene diamine. Aromatic anthramine refers to a compound in which a diarylamino group is directly attached to anthracene, most preferably at position 9. Aromatic anthradiamine refers to a compound in which two diarylamino groups are directly attached to anthracene, most preferably at positions 9, 10. Aromatic pyrene amines, aromatic pyrene diamines, aromatic chrysene amines and aromatic chrysene diamine are similarly defined, wherein the diarylarylamino group is most preferably attached to position 1 or 1 and 6 of pyrene.

Examples of singlet emitter based on vinylamine and arylamine are also preferred examples which may be found in the following patent documents: WO 2006/000388, WO 2006/058737, WO 2006/000389, WO 2007/065549, WO 2007/115610, U.S. Pat. No. 7,250,532 B2, DE 102005058557 A1, CN 1583691 A, JP 08053397 A, U.S. Pat. No. 6,251,531 B1, US 2006/210830 A, EP 1957606 A1, and US 2008/0113101 A1, the whole contents of which are incorporated herein by reference.

Examples of singlet light emitters based on distyrylbenzene and its derivatives may be found in, for example, U.S. Pat. No. 5,121,029.

Further preferred singlet emitters may be selected from the group consisting of: indenofluorene-amine and indenofluorene-diamine such as disclosed in WO 2006/122630, benzoindenofluorene-amine and benzoindenofluorene-diamine such as disclosed in WO 2008/006449, dibenzoindenofluorene-amine and dibenzoindenofluorene-diamine such as disclosed in WO2007/140847.

Other materials useful as singlet emissors include, but not limited to, polycyclic aromatic compounds, especially any one selected from the derivatives of the following compounds: anthracenes such as 9,10-di-naphthylanthracene, naphthalene, tetraphenyl, oxyanthene, phenanthrene, perylene such as 2,5,8,11-tetra-t-butylatedylene, indenoperylene, phenylenes such as 4,4'-(bis (9-ethyl-3-carbazovinylene)-1,1'-biphenyl, periflanthene, decacyclene, coronene, fluorene, spirobifluorene, arylpyren (e.g., US20060222886), arylenevinylene (e.g., U.S. Pat. Nos. 5,121,029, 5,130,603), cyclopentadiene such as tetraphenylcyclopentadiene, rubrene, coumarine, rhodamine, quinacridone, pyrane such as 4 (dicyanoethylene)-6-(4-dimethylaminostyryl-2-methyl)-4H-pyrane (DCM), thiapyran, bis (azinyl) imine-boron compounds (US 2007/0092753 A1), bis (azinyl) methene compounds, carbostyryl compounds, oxazone, benzoxazole, benzothiazole, benzimidazole, and diketopyrrolopyrrole. Examples of some singlet emitter materials may be found in the following patent documents: U.S. Pat. Nos. 4,769,292, 6,020,078, US 2007/0252517 A1, and US 2007/0252517 A1, the whole contents of which are incorporated herein by reference.

Examples of suitable singlet emitters are listed below:

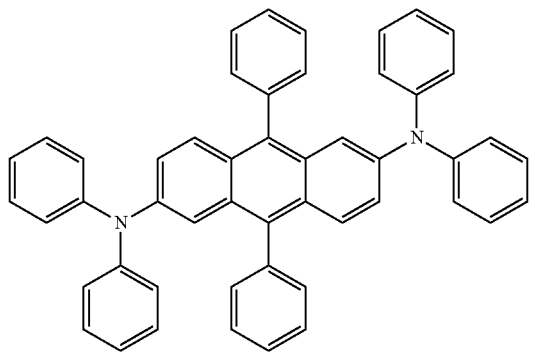

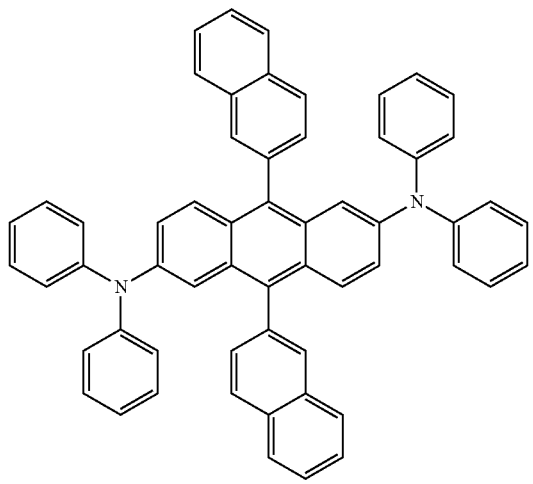

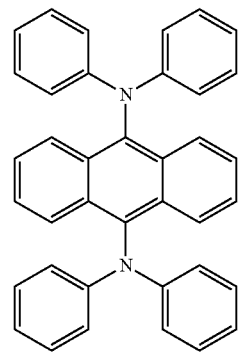

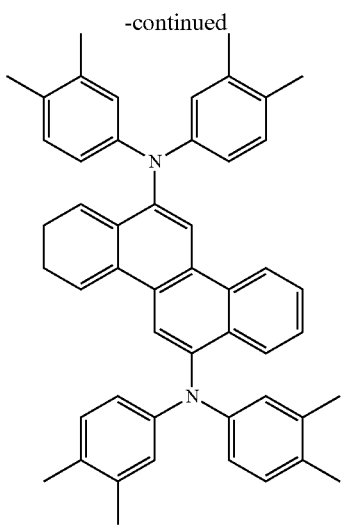

6. Polymers

In some embodiments, the organic functional materials described above, including HIM, HTM, ETM, EIM, Host, fluorescent emitter, and phosphorescent emitters, may be in the form of polymers.

In a preferred embodiment, the polymer suitable for the present disclosure is a conjugated polymer. In general, the conjugated polymer may have the general formula:

Chemical formula 1 wherein B, A may be independently selected as the same or different structural units in multiple occurrences.

B: a π-conjugated structural unit with relatively large energy gap, also referred to as backbone unit, which may be selected from monocyclic or polycyclic aryl or heteroaryl, preferably in the form of benzene, biphenylene, naphthalene, anthracene, phenanthrene, dihydrophenanthrene, 9,10-dihydrophenanthroline, fluorene, difluorene, spirobifluorene, p-phenylenevinylene, trans-indenofluorene, cis-indenofluorene, dibenzol-indenofluorene, indenonaphthalene and derivatives thereof.

A: a π-conjugated structural unit with relatively small energy gap, also referred to as a functional unit, which, according to different functional requirements, may be selected from the above-mentioned hole-injection or hole-transport material (HIM/HTM), hole-blocking material (HBM), electron-injection or electron-transport material (EIM/ETM), electron-blocking material (EBM), organic host material (Host), singlet emitter (fluorescent emitter), multiplet emitter (phosphorescent emitter).

x,y: >0, and x+y=1.

In a preferred embodiment, the polymer HTM material is a homopolymer, and the preferred homopolymer is selected from the group consisting of polythiophene, polypyrrole, polyaniline, polybenzene triarylamine, polyvinylcarbazole and their derivatives.

In another preferred embodiment, the polymer HTM material is a conjugated copolymer represented by Chemical Formula 1, wherein A: a functional group having a hole transporting capacity, which may be selected from structural units comprising the above-mentioned hole-injection or hole-transport material (HIM/HTM); in a preferred embodiment, A is selected from the group consisting of amine, benzenesulfonates, thiophenes and thiophenes such as dithienothiophene and thiophene, pyrrole, aniline, carbazole, indolecarbazole, indenobenzofluorene, pentacene, phthalocyanine, porphyrins and their derivatives.

x,y: >0, and x+y=1; usually y≥0.10, preferably ≥0.15, more preferably ≥0.20, preferably x=y=0.5.

Examples of suitable conjugated polymers that can be used as HTM are listed below:

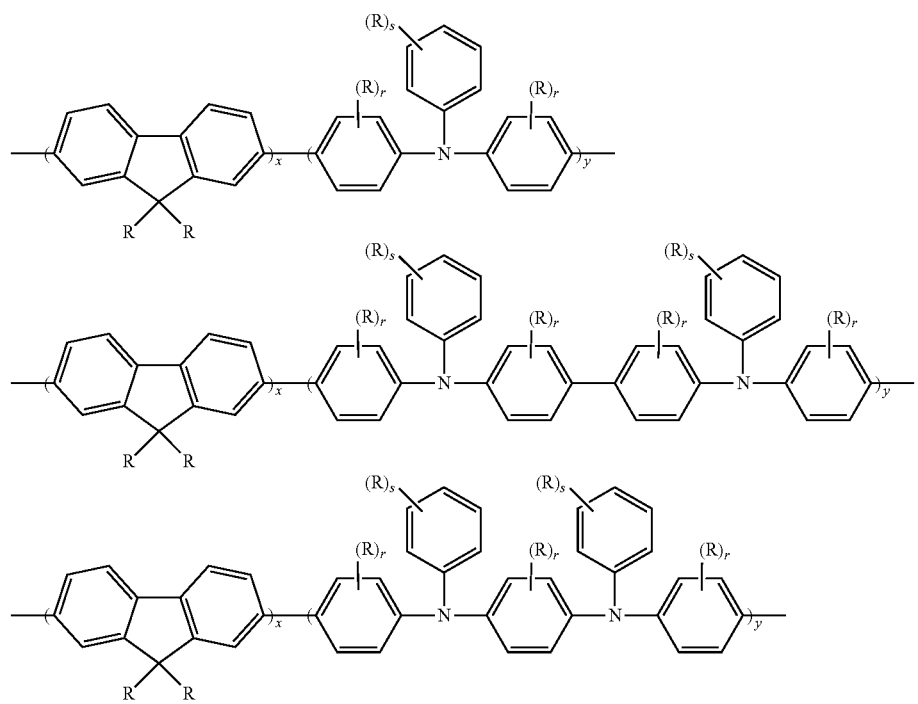

-continued

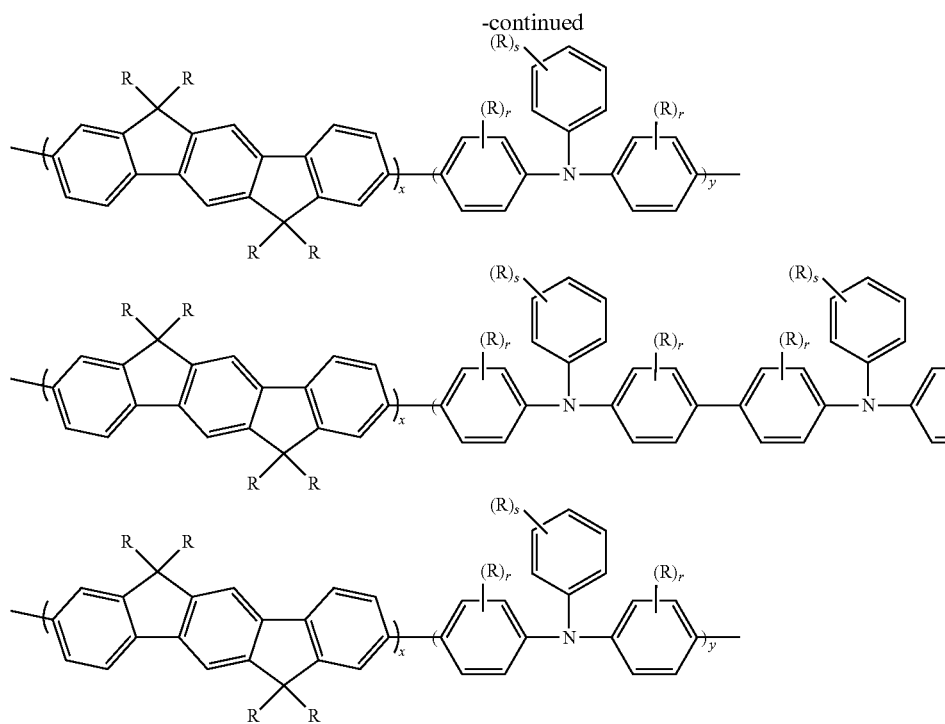

wherein R are each independently hydrogen; a straight chain alkyl group, an alkoxy group or a thioalkoxy group having 1 to 20 C atoms; a branched or cyclic alkyl group, an alkoxy group or a thioalkoxy group or a silyl group having 3 to 20 C atoms; or a substituted keto group having 1 to 20 C atoms; an alkoxycarbonyl group having 2 to 20 C atoms; aryloxycarbonyl group having 7 to 20 C atoms; a cyano group (—CN); a carbamoyl group (—C(=O)NH$_2$); a haloyl group (—C(=O)—X wherein X represents a halogen atom); a formyl group (—C(=O)—H); an isocyanato group; an isocyanate group; a thiocyanate group; an isothiocyanate group; a hydroxyl group; a nitro group; a CF$_3$ group; Cl; Br; F; a crosslinkable group; a substituted or unsubstituted aromatic or heteroaromatic ring system having 5 to 40 ring atoms; or an aryloxy or heteroaryloxy group having 5 to 40 ring atoms, or a combination of these systems in which one or more groups R may form a single ring or polycyclic aliphatic or aromatic ring system between one another and/or with a ring bonded to the group R;

r is 0, 1, 2, 3 or 4;

s is 0, 1, 2, 3, 4 or 5;

x,y: >0, and x+y=1; usually y=y≥0.10, preferably ≥0.15, more preferably ≥0.20, preferably x=y=0.5.

Another preferred type of organic ETM material is a polymer having an electron transporting capacity comprising a conjugated polymer and a nonconjugated polymer.

The preferred polymer ETM material is a homopolymer, which is selected from the group consisting of polyphenanthrene, polyphenanthroline, polyindenyl fluorene, poly spiethylene fluorene, polyfluorene and their derivatives.

The preferred polymer ETM material is a conjugated copolymer represented by Chemical Formula 1, wherein A can be independently selected in the same or different forms in multiple occurrences:

A: a functional group having a electron transporting capacity, preferably selected from the group consisting of tris (8-quinolinolato) aluminum, benzene, biphenylene, naphthalene, anthracene, phenanthrene, dihydrophenanthrene, fluorene, difluorene, spirobifluorene, p-phenylenevinylene, pyrene, perylene, 9,10-dihydrophenanthroline, phenoxazine, phenanthroline, trans-indenofluorene, cis-indenonfluorene, dibenzol-indenofluorene, indenonaphthalene, benzanthracene and their derivatives.

x,y: >0, and x+y=1; usually y≥0.10, preferably ≥0.15, more preferably ≥0.20, preferably x=y=0.5.

In a preferred embodiment, light-emitting polymers are conjugated polymers having the following formula:

Chemical formula 2

B: as defined in chemical formula 1.

A1: a functional group having a hole or electron transporting capacity, which may be selected from structural units of the above-mentioned hole-injection or hole-transport material (HIM/HTM), or electron injection or transport material.

A2: a group having light emitting function, which may be selected from structural units of singlet emitter (fluorescent emitter) or multiplet emitter (phosphorescent emitter).

x,y,z: >0, and x+y+z=1;

Examples of light-emitting polymers are disclosed in the following patent applications: WO2007043495, WO2006118345, WO2006114364, WO2006062226, WO2006052457, WO2005104264, WO2005056633, WO2005033174, WO2004113412, WO2004041901, WO2003099 901, WO2003051092, WO2003020790, US20040076853, US20040002576, US2007208567, U.S. Pat. No. 5,962,631, EP201345477, EP20031344788 and DE102004020298, the whole contents of which are incorporated herein by reference.

In another embodiment, the polymers suitable for the present disclosure may be non-conjugated polymers. The nonconjugated polymer may be the backbone with all functional groups on the side chain. Examples of such nonconjugated polymers for use as phosphorescent host or phosphorescent emitter materials may be found in patent applications such as U.S. Pat. No. 7,250,226 B2, JP2007059939A, JP2007211243A2 and JP2007197574A2. Examples of such nonconjugated polymers used as fluorescent light-emitting materials may be found in the patent applications JP2005108556, JP2005285661, and JP2003338375. In addition, the non-conjugated polymer may also be a polymer, with the conjugated functional units on the backbone linked by non-conjugated linking units. Examples of such polymers are disclosed in DE102009023154.4 and DE102009023156.0. The whole contents of the above mentioned patent documents are incorporated herein by reference.

In some embodiments, the metal organic complex is present in an amount of from 0.01 to 30 wt %, preferably from 0.1 to 20 wt %, more preferably from 0.2 to 15 wt %, most preferably from 2 to 15 wt %, based on the mixture of the present disclosure.

In a preferred embodiment, the mixture according to the present disclosure comprises an organic metal complex according to the present disclosure and the triplet host material as described above.

In another preferred embodiment, the mixture according to the present disclosure comprises a metal organic complex according to the present disclosure, the triplet host material as described above and another organic metal complex.

The present disclosure further relates to a formulation comprising the organic metal complex or the polymer or the mixture, and at least one organic solvent. The present disclosure further relates to a film comprising the organic metal complex or the polymer according to the present disclosure prepared from solution.

Examples of the organic solvents include, but not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxahexane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, naphthane, indene and/or their mixtures.

In a preferred embodiment, the formulation according to the present disclosure is a solution.

In another preferred embodiment, the formulation according to the present disclosure is a suspension.

The formulation in the examples of the present disclosure may comprise an organic metal complex or a polymer or their mixture from 0.01 to 20 wt %, more preferably from 0.1 to 15 wt %, more preferably from 0.2 to 10 wt %, and most preferably from 0.25 to 5 wt %.

The present disclosure also relates to the use of said formulation as a coating or printing ink in the preparation of organic electronic devices, and particularly preferably by means of printing or coating in a preparation process.

Among them, suitable printing or coating techniques may include, but not limited to, ink-jet printing, nozzle printing, typography, screen printing, dip coating, spin coating, blade coating, roll printing, torsion printing, lithography, flexography, rotary printing, spray coating, brush coating or pad printing, slit type extrusion coating, and so on. Preferred are gravure printing, slit type extrusion coating, nozzle printing and inkjet printing. The solution or suspension may additionally comprise one or more components such as surface active compounds, lubricants, wetting agents, dispersing agents, hydrophobic agents, binders, etc., for adjusting viscosity, film forming properties, improving adhesion, and the like. For more information about printing techniques and their requirements for solutions, such as solvent, concentration, viscosity, etc., see Handbook of Print Media: Technologies and Production Methods, edited by Helmut Kipphan, ISBN 3-540-67326-1.

Based on the above polymers, the present disclosure also provides application of the organic metal complexes or polymers as described above in an organic electronic device, which may be selected from, but not limited to, organic light emitting diodes (OLED), organic photovoltaics (OPVs), organic light emitting electrochemical cells (OLEEC), organic field effect transistor (OFET), organic light emitting field effectors, organic lasers, organic spintronic devices, organic sensors, and organic plasmon emitting diodes, especially OLED. In an embodiment of the present disclosure, the organic metal polymer is preferably used in a light-emitting layer of a OLED device.

The present disclosure further provides an organic electronic device which may comprise at least one organic metal complex or polymer as described above. Typically, such an organic electronic device may comprise at least a cathode, an anode, and a functional layer between the cathode and the anode, wherein the functional layer may comprise at least one organic metal complex as described above. The organic electronic device may be selected from, but not limited to, organic light emitting diodes (OLED), organic photovoltaics (OPVs), organic light emitting electrochemical cells (OLEEC), organic field effect transistor (OFET), organic light emitting field effectors, organic lasers, organic spintronic devices, organic sensors, and organic plasmon emitting diodes.

In a particularly preferred embodiment, the organic electronic device, especially OLED may include a substrate, an anode, at least one light-emitting layer, and a cathode.

The substrate may be opaque or transparent. Transparent substrates may be used to make transparent light-emitting components. See, for example, Bulovic et al., Nature 1996, 380, p 29, and Gu et al., Appl. Phys. Lett. 1996, 68, p 2606. The substrate may be rigid or flexible. The substrate may be plastic, metal, semiconductor wafer or glass. Most preferably the substrate has a smooth surface. Substrates free of surface defects are particularly desirable. In a preferred embodiment, the substrate is flexible and may be selected from polymer films or plastic, with a glass transition temperature (Tg) of 150° C. or above, more preferably above 200° C., more preferably above 250° C., and most preferably above 300° C. Examples of suitable flexible substrates are poly (ethylene terephthalate) (PET) and polyethylene glycol (2,6-naphthalene) (PEN).

The anode may comprise a conductive metal or a metal oxide, or a conductive polymer. The anode may easily inject holes into the hole-injection layer (HIL) or the hole-transport layer (HTL) or the light-emitting layer. In one embodiment, the absolute value of the difference between the work function of the anode and the HOMO energy level or the valence band energy level of the emitter in the light-emitting layer or of the p-type semiconductor material of the HIL or HTL or the electron-blocking layer (EBL) may be smaller than 0.5 eV, more preferably smaller than 0.3 eV, and most preferably smaller than 0.2 eV. Examples of anode materials may include, but not limited to, Al, Cu, Au, Ag, Mg, Fe, Co, Ni, Mn, Pd, Pt, ITO, aluminum-doped zinc oxide (AZO), and the like. Other suitable anode materials are known and may be readily selected for use by a person skilled in the art.

The anode material may be deposited using any suitable technique, such as suitable physical vapor deposition, including RF magnetron sputtering, vacuum thermal evaporation, electron beam (e-beam), and the like. In some embodiments, the anode may be patterned. The patterned ITO conductive substrate is commercially available and may be used to fabricate the device according to the disclosure.

The cathode may comprise a conductive metal or a metal oxide. The cathode may easily inject electrons into the EIL or ETL or directly into the light-emitting layer. In one embodiment, the absolute value of the difference between the work function of the cathode and the LUMO energy level or the valence band energy level of the emitter in the light-emitting layer or of the n-type semiconductor material of the electron-injection layer (EIL) or the electron-transport layer (ETL) or the hole-blocking layer (HBL) may be smaller than 0.5 eV, more preferably smaller than 0.3 eV, and most preferably smaller than 0.2 eV. In principle, all of the material that may be used as the cathode of an OLED may serve as a cathode material for the device of the present disclosure. Examples of the cathode material may include, but not limited to, Al, Au, Ag, Ca, Ba, Mg, LiF/Al, MgAg alloys, BaF2/Al, Cu, Fe, Co, Ni, Mn, Pd, Pt, ITO, and the like. The cathode material may be deposited using any suitable technique, such as suitable physical vapor deposition, including RF magnetron sputtering, vacuum thermal evaporation, electron beam (e-beam), and the like.

OLEDs may also comprise other functional layers such as hole-injection layer (HIL), hole-transport layer (HTL), electron-blocking layer (EBL), electron-injection layer (EIL), electron-transport layer (ETL), and hole-blocking layer (HBL). Materials suitable for use in these functional layers are described in detail as before.

In a preferred embodiment, in the light emitting device according to the present disclosure, the light-emitting layer thereof comprises the organic metal complex or polymer of the present disclosure and may be prepared by a solution processing method.

The light emitting device according to the present disclosure may have a light emission wavelength between 300 and 1000 nm, more preferably between 350 and 900 nm, and more preferably between 400 and 800 nm.

The present disclosure also relates to the use of organic electronic devices according to the present disclosure in a variety of electronic devices including, but not limited to, display devices, lighting devices, light sources, sensors, and the like.

The disclosure will now be described with reference to the preferred embodiments, but the disclosure is not to be construed as being limited to the following examples. It is to be understood that the appended claims are intended to cover the scope of the disclosure. A person skilled in the art will understand that modifications can be made to various embodiments of the present disclosure with the teaching of the present disclosure, which will be covered by the spirit and scope of the claims of the disclosure.

EXAMPLES

1. Metal Organic Complexes and their Energy Structures

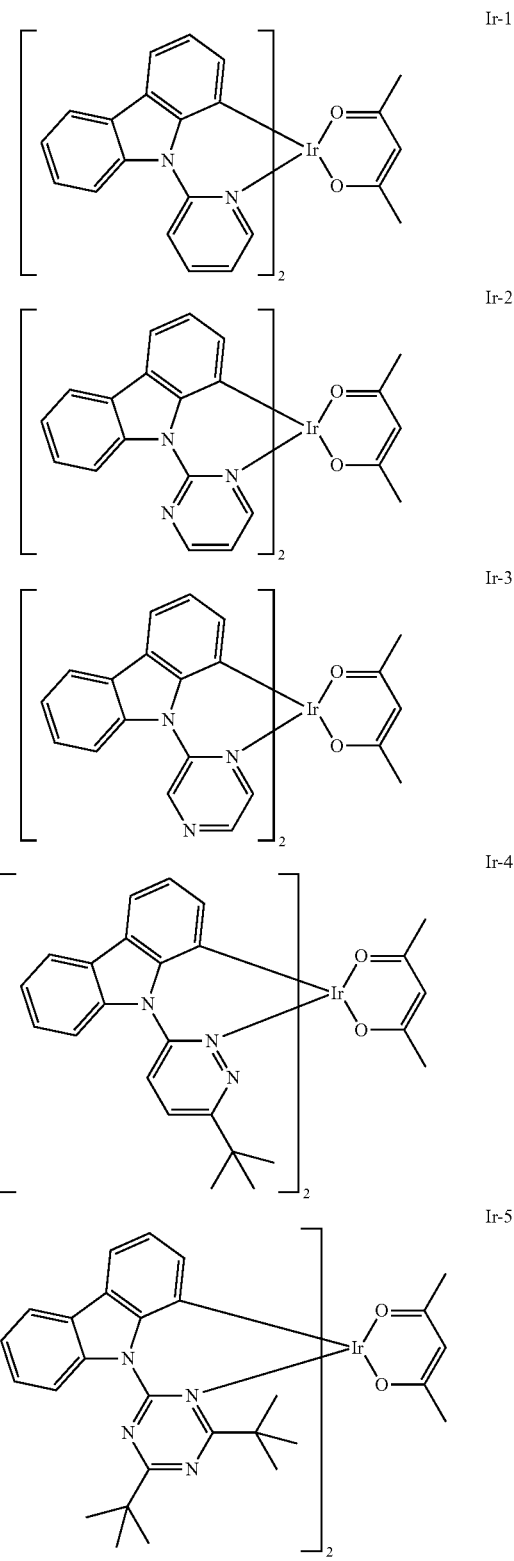

The energy level of the metal organic complex Ir-1-Ir-5 can be obtained by quantum computation, for example, by using TD-DFT (time-dependent density functional theory) by Gaussian03W (Gaussian Inc.), and specific simulation methods can be found in WO2011141110. First, the molecular geometry is optimized by semi-empirical method "Ground State/Hartree-Fock/Default Spin/LanL2MB" (Charge 0/Spin Singlet), and then the energy structure of organic molecules is determined by TD-DFT (time-dependent density functional theory) Count "TD-SCF/DFT/Default Spin/B3PW91/gen geom=communication pseudo=lanl2" (Charge 0/Spin Singlet). The HOMO and LUMO energy levels are calculated using the following calibration formula, and S1 and T1 are used directly.

$$HOMO(eV)=((HOMO(Gaussian) \times 27.212)-0.9899)/1.1206$$

$$LUMO(eV)=((LUMO(Gaussian) \times 27.212)-2.0041)/1.385$$

Wherein, HOMO (G) and LUMO (G) are the direct results of Gaussian 03W, in units of Hartree. The results are shown in Table 1:

TABLE 1

| Materials | HOMO [eV] | LUMO [eV] | T1 [eV] | S1 [eV] |
|---|---|---|---|---|
| Ir-1 | −5.18 | −2.47 | 2.59 | 2.70 |
| Ir-2 | −5.33 | −2.77 | 2.39 | 2.47 |
| Ir-3 | −5.47 | −3.04 | 2.13 | 2.25 |
| Ir-4 | −5.04 | −2.80 | 2.01 | 2.09 |
| Ir-5 | −5.45 | −2.67 | 2.61 | 2.74 |

2. Synthesis of the Organic Metal Complexes

The synthesis of metal organic complexes is as follows:

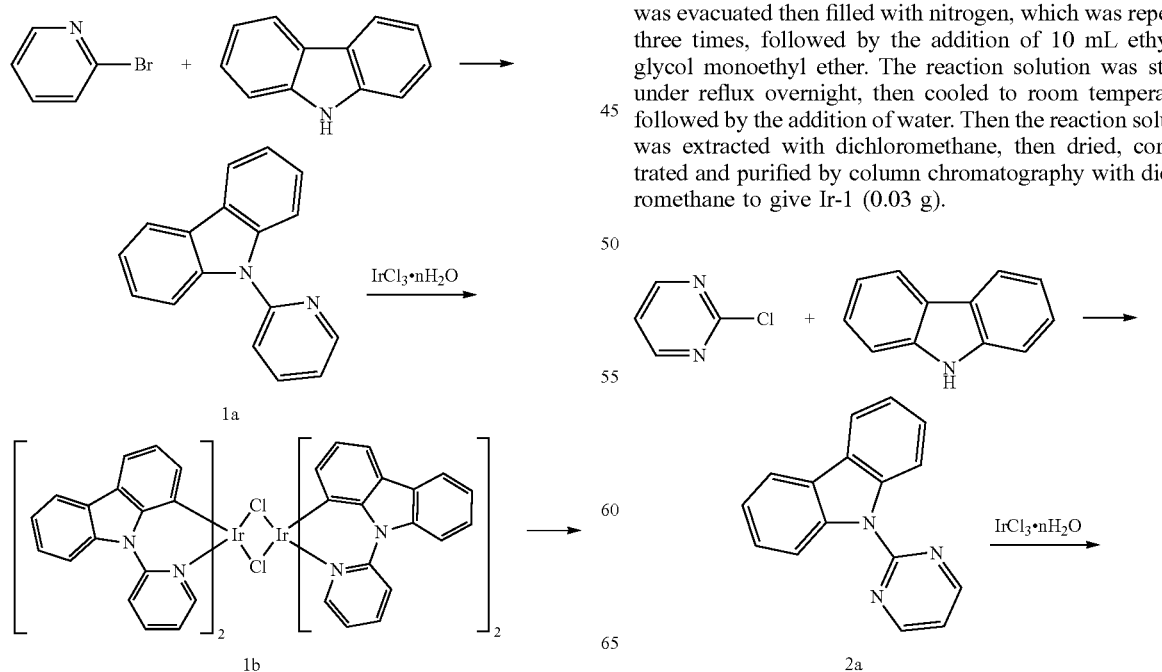

Synthesis of Intermediate 1a

Carbazole (1.67 g, 10 mmol), cuprous iodide (19 mg, 0.1 mmol), potassium carbonate (2.76 g, 0.02 mol), 2-bromopyridine (1.896 g, 0.012 mol) and DMF 20 mL were refluxed for 24 h under nitrogen and then cooled to room temperature. Water was added to the reaction solution, and then the reaction solution was extracted with ethyl acetate. The organic phase was washed with water, then dried with anhydrous magnesium sulfate, concentrated, and recrystallized from ethanol to give 1a (1.5 g).

Synthesis of Intermediate 1b

The intermediate 1a (0.39 g, 1.6 mmol) and iridium trichloride hydrate (0.23 g, 0.66 mmol) were put in a dry two-necked flask. Then the two-necked flask was evacuated then filled with nitrogen, which was repeated three times, followed by the addition of a mixture solution of 10 mL of ethylene glycol monoethyl ether and 3 mL of water. The reaction solution was stirred at 110° C. for 24 hours, then cooled to room temperature, filtered, washed with n-hexane and dried, without further purification.

Synthesis Example 1: Synthesis of Compound Ir-1

The intermediate 1b (0.14 g, 0.1 mmol), acetylacetone (0.1 mL, 1 mmol) and Na$_2$CO$_3$ (0.106 g, 1 mmol) were placed in a dry two-necked flask. Then the two-necked flask was evacuated then filled with nitrogen, which was repeated three times, followed by the addition of 10 mL ethylene glycol monoethyl ether. The reaction solution was stirred under reflux overnight, then cooled to room temperature, followed by the addition of water. Then the reaction solution was extracted with dichloromethane, then dried, concentrated and purified by column chromatography with dichloromethane to give Ir-1 (0.03 g).

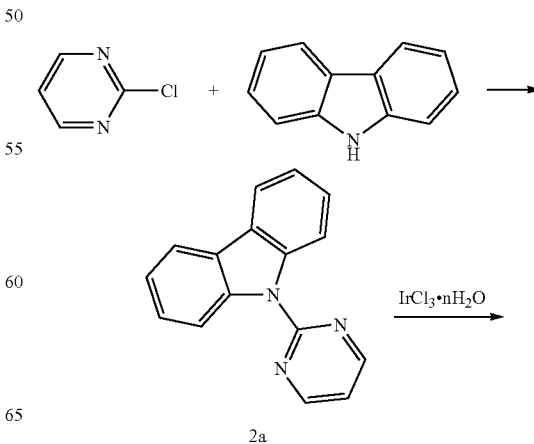

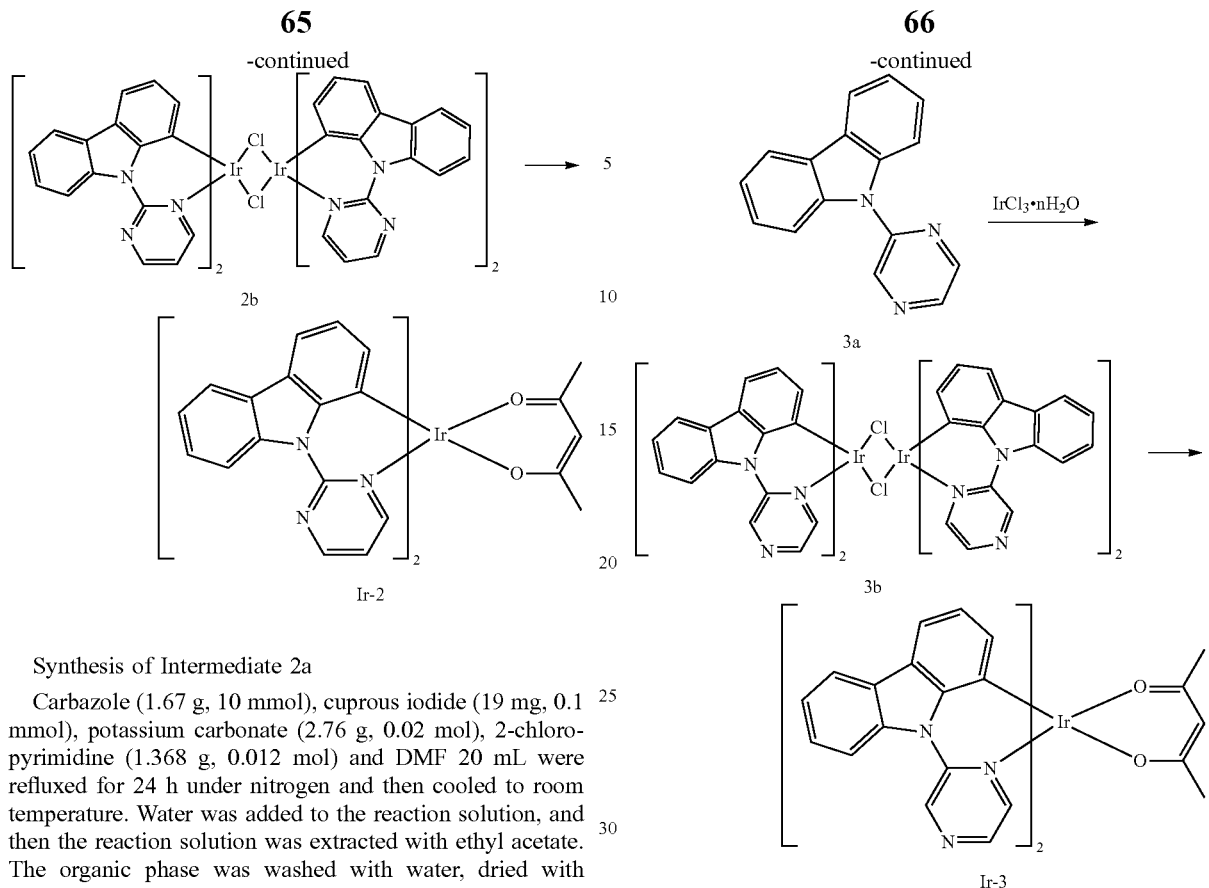

Synthesis of Intermediate 2a

Carbazole (1.67 g, 10 mmol), cuprous iodide (19 mg, 0.1 mmol), potassium carbonate (2.76 g, 0.02 mol), 2-chloropyrimidine (1.368 g, 0.012 mol) and DMF 20 mL were refluxed for 24 h under nitrogen and then cooled to room temperature. Water was added to the reaction solution, and then the reaction solution was extracted with ethyl acetate. The organic phase was washed with water, dried with anhydrous magnesium sulfate, concentrated, and recrystallized from ethanol to give 2a (1.5 g).

Synthesis of intermediate 2b

The intermediate 2a (0.39 g, 1.6 mmol) and iridium trichloride hydrate (0.23 g, 0.66 mmol) were placed in a dry two-necked flask. Then the dry two-necked flask was evacuated then filled with nitrogen, which was repeated three times, followed by the addition of a mixture solution of 10 mL of ethylene glycol monoethyl ether and 3 mL of water. The reaction solution was stirred at 110° C. for 24 hours, cooled to room temperature, filtered, washed with n-hexane and dried, without further purification.

Synthesis Example 2: Synthesis of Compound Ir-2

The intermediate 2b (0.14 g, 0.1 mmol), acetylacetone (0.1 mL, 1 mmol), $Na_2CO_3$ (0.106 g, 1 mmol) were placed in a dry two-necked flask. Then the two-necked flask was evacuated then filled with nitrogen, which was repeated three times, followed by the addition of 10 mL ethylene glycol monoethyl ether. The reaction solution was stirred under reflux overnight, then cooled to room temperature, followed by the addition of water. Then the reaction solution was extracted with dichloromethane, then dried, concentrated and purified by column chromatography with dichloromethane to give Ir-2 (0.025 g).

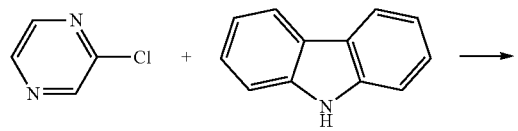

Synthesis of Intermediate 3a

Carbazole (0.67 g, 10 mmol), cuprous iodide (19 mg, 0.1 mmol), potassium carbonate (2.76 g, 0.02 mol), 2-chloropyrazine (1.368 g, 0.012 mol) and DMF 20 mL were refluxed for 24 h under nitrogen and then cooled to room temperature. Water was added to the reaction solution, and then the reaction solution was extracted with ethyl acetate. The organic phase was washed with water, then dried with anhydrous magnesium sulfate, concentrated, and then recrystallized from ethanol to give 2a (1.5 g).

Synthesis of Intermediate 3b

The intermediate 3a (0.39 g, 1.6 mmol) and iridium trichloride hydrate (0.23 g, 0.66 mmol) were placed in a dry two-necked flask. Then the two-necked flask was evacuated then filled with nitrogen, which was repeated three times, followed by the addition of a mixture solution of 10 mL of ethylene glycol monoethyl ether and 3 mL of water. Then the reaction solution was stirred at 110° C. for 24 hours, cooled to room temperature, filtered, washed with n-hexane and dried, without further purification.

Synthesis Example 3: Synthesis of Compound Ir-3

The intermediate 3b (0.14 g, 0.1 mmol), acetylacetone (0.1 mL, 1 mmol) and $Na_2CO_3$ (0.106 g, 1 mmol) were placed in a dry two-necked flask. Then the two-necked flask was evacuated then filled with nitrogen, which was repeated three times, followed by the addition of 10 mL ethylene glycol monoethyl ether, stirred under reflux overnight, cooled to room temperature, followed by the addition of water. Then the reaction solution was extracted with dichloromethane, then dried, concentrated and purified with dichloromethane to give Ir-3 (0.025 g).

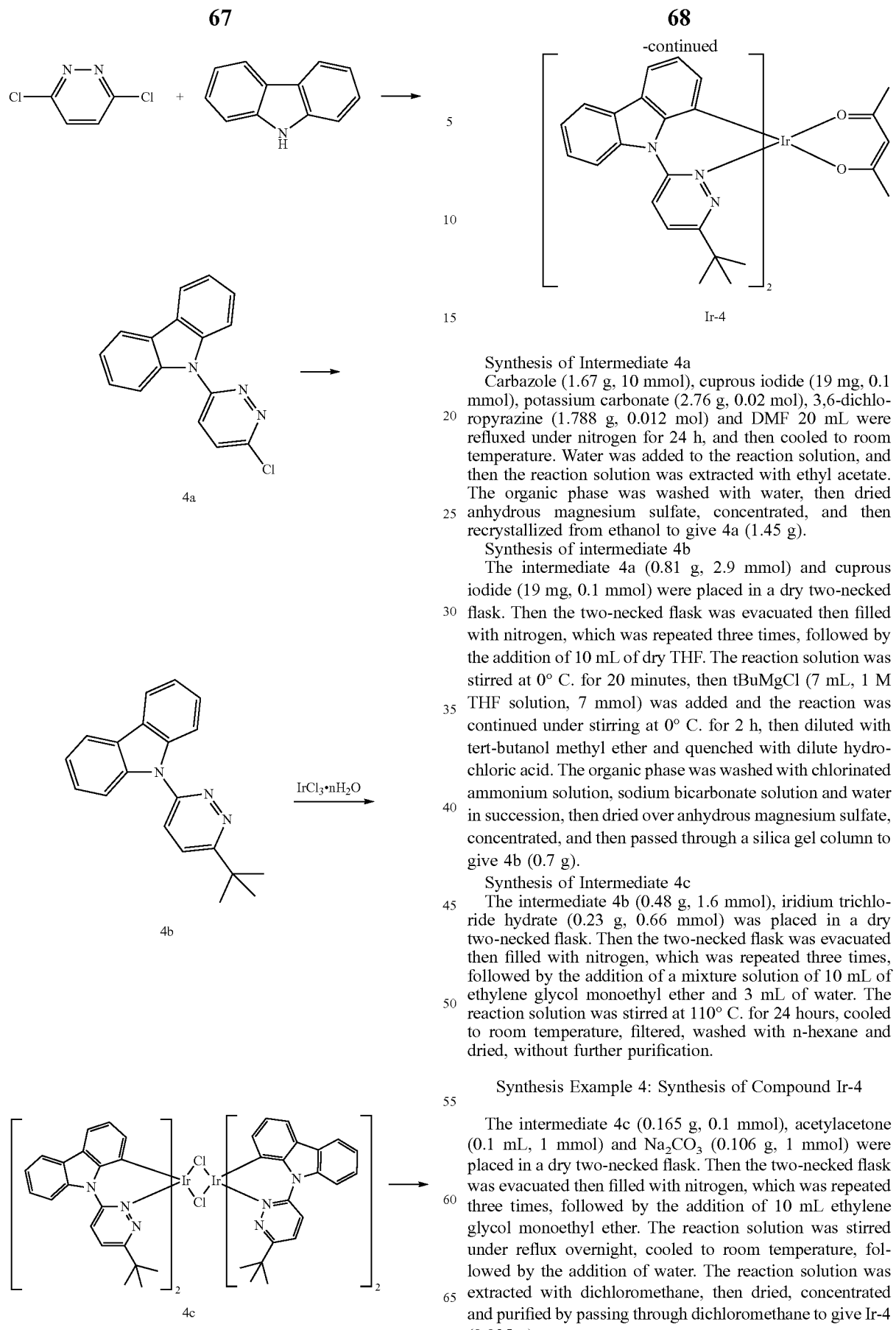

Synthesis of Intermediate 4a

Carbazole (1.67 g, 10 mmol), cuprous iodide (19 mg, 0.1 mmol), potassium carbonate (2.76 g, 0.02 mol), 3,6-dichloropyrazine (1.788 g, 0.012 mol) and DMF 20 mL were refluxed under nitrogen for 24 h, and then cooled to room temperature. Water was added to the reaction solution, and then the reaction solution was extracted with ethyl acetate. The organic phase was washed with water, then dried anhydrous magnesium sulfate, concentrated, and then recrystallized from ethanol to give 4a (1.45 g).

Synthesis of intermediate 4b

The intermediate 4a (0.81 g, 2.9 mmol) and cuprous iodide (19 mg, 0.1 mmol) were placed in a dry two-necked flask. Then the two-necked flask was evacuated then filled with nitrogen, which was repeated three times, followed by the addition of 10 mL of dry THF. The reaction solution was stirred at 0° C. for 20 minutes, then tBuMgCl (7 mL, 1 M THF solution, 7 mmol) was added and the reaction was continued under stirring at 0° C. for 2 h, then diluted with tert-butanol methyl ether and quenched with dilute hydrochloric acid. The organic phase was washed with chlorinated ammonium solution, sodium bicarbonate solution and water in succession, then dried over anhydrous magnesium sulfate, concentrated, and then passed through a silica gel column to give 4b (0.7 g).

Synthesis of Intermediate 4c

The intermediate 4b (0.48 g, 1.6 mmol), iridium trichloride hydrate (0.23 g, 0.66 mmol) was placed in a dry two-necked flask. Then the two-necked flask was evacuated then filled with nitrogen, which was repeated three times, followed by the addition of a mixture solution of 10 mL of ethylene glycol monoethyl ether and 3 mL of water. The reaction solution was stirred at 110° C. for 24 hours, cooled to room temperature, filtered, washed with n-hexane and dried, without further purification.

Synthesis Example 4: Synthesis of Compound Ir-4

The intermediate 4c (0.165 g, 0.1 mmol), acetylacetone (0.1 mL, 1 mmol) and $Na_2CO_3$ (0.106 g, 1 mmol) were placed in a dry two-necked flask. Then the two-necked flask was evacuated then filled with nitrogen, which was repeated three times, followed by the addition of 10 mL ethylene glycol monoethyl ether. The reaction solution was stirred under reflux overnight, cooled to room temperature, followed by the addition of water. The reaction solution was extracted with dichloromethane, then dried, concentrated and purified by passing through dichloromethane to give Ir-4 (0.025 g).

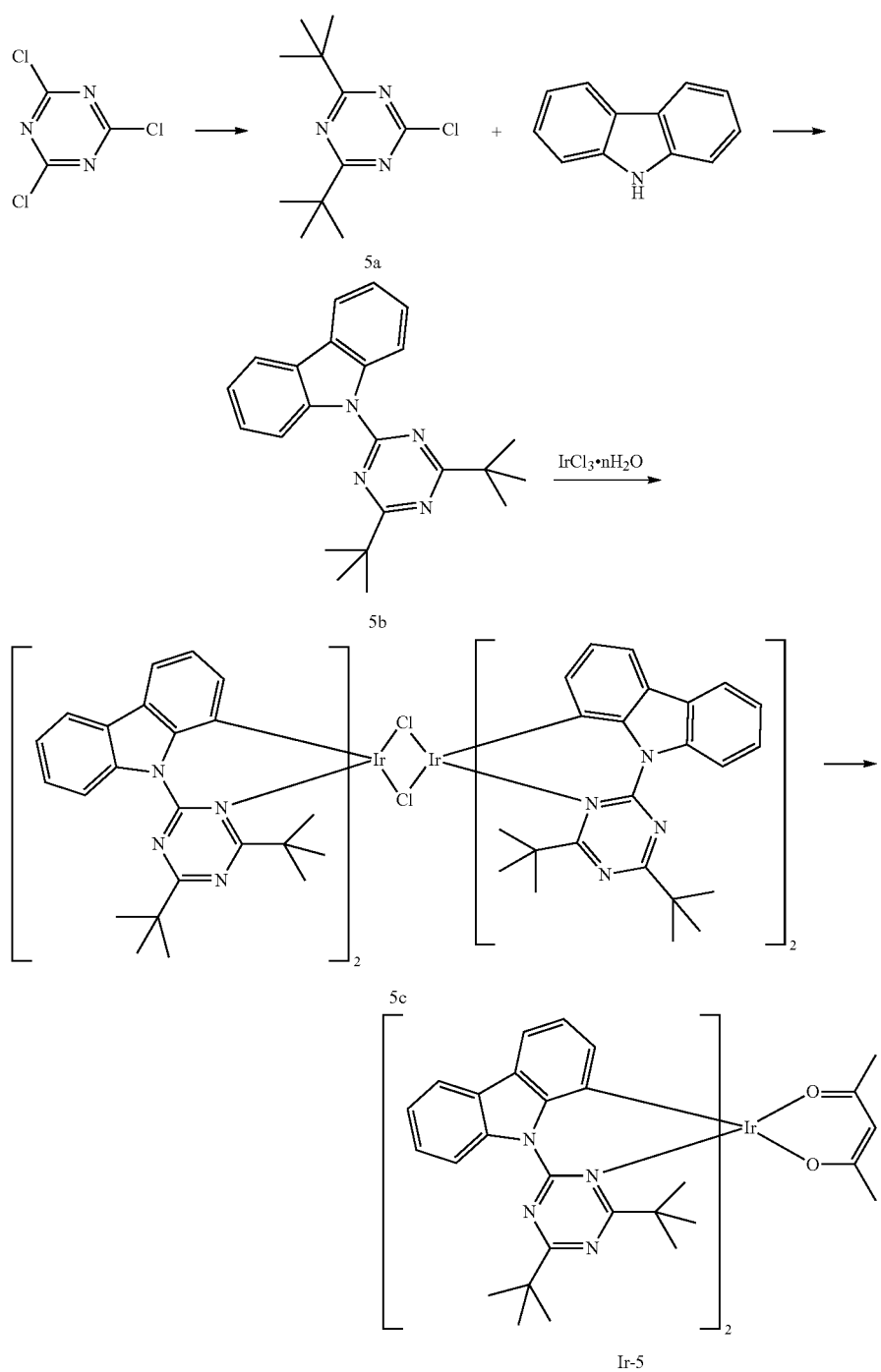

Synthesis of Intermediate 5a

Trichlorotriazine (5.35 g, 29 mmol) and cuprous iodide (190 mg, 1 mmol) were placed in a dry two-necked flask. Then the two-necked flask was evacuated then filled with nitrogen, which was repeated three times, followed by the addition of 20 mL of dry THF. After stirring for 20 minutes at 0° C., tBuMgCl (70 mL, 1 M THF solution, 70 mmol) was added and the reaction was continued at 0° C. for 2 h under stirring. Then the reaction was diluted with tert-butanol methyl ether and quenched with dilute hydrochloric acid. The organic phase was washed with ammonium chloride solution, sodium bicarbonate solution and water in succession, then dried over anhydrous magnesium sulfate, concentrated, and then passed through a silica gel column to give 5a (5.8 g).

Synthesis of Intermediate 5b

Carbazole (1.67 g, 10 mmol), cuprous iodide (19 mg, 0.1 mmol), potassium carbonate (2.76 g, 0.02 mol), intermediate 5a (2.72 g, 0.012 mol) and DMF 20 mL were refluxed under nitrogen for 24 h, and then cooled to room temperature. Water was added to the reaction solution and the reaction solution was extracted with ethyl acetate. The organic phase was washed with water, dried over anhydrous magnesium sulfate, concentrated, and then recrystallized from ethanol to give 5b (2.8 g).

Synthesis of Intermediate 5c

The intermediate 5b (0.57 g, 1.6 mmol) and iridium trichloride hydrate (0.23 g, 0.66 mmol) were placed in a dry two-necked flask. Then the two-necked flask was evacuated then filled with nitrogen, which was repeated three times, followed by the addition of a mixture solution of 10 mL of ethylene glycol monoethyl ether and 3 mL of water. The reaction solution was stirred at 110° C. for 24 hours, cooled to room temperature, filtered, washed with n-hexane and dried, without further purification.

Synthesis Example 5: Synthesis of Compound Ir-5

The intermediate 5c (0.188 g, 0.1 mmol), acetylacetone (0.1 mL, 1 mmol), Na$_2$CO$_3$ (0.106 g, 1 mmol) were placed in a dry two-necked flask. Then the two-necked flask was evacuated then filled with nitrogen, which was repeated three times, followed by the addition of 10 mL ethylene glycol monoethyl ether. The reaction solution was stirred under reflux overnight, cooled to room temperature, followed by the addition of water. The reaction solution was extracted dichloromethane, then dried, concentrated and purified with dichloromethane column to give Ir-5 (0.038 g).

3. Preparation and Characterization of OLED Devices:

The preparation steps of OLED devices having ITO/NPD (60 nm)/15% Ir-1 to Ir-5: mCP (15 nm)/TPBi (65 nm)/LiF (1 nm)/Al (150 nm)/cathode are as follows:

a. cleaning of a conductive glass substrate: when used for the first time, a variety of solvents may be used for cleaning, such as chloroform, ketone, isopropyl alcohol, and then UV ozone plasma treatment was carried out;

b. HTL (60 nm), EML (25 nm), ETL (65 nm): by hot vapor deposition in high vacuum (1×10-6 mbar, mbar);

c. cathode: LiF/Al (1 nm/150 nm) being prepared by hot vapor deposition in high vacuum (1×10$^6$ mbar);

d. package: device was packaged with UV curing resin in the nitrogen glove box.

The current-voltage-luminance (JVL) characteristics of each OLED device are characterized by characterization equipment, while important parameters such as efficiency and external quantum efficiency were recorded. After detection, maximum external quantum efficiency of OLEDx (corresponding to metal organic Ir-x) reaches more than 10%.

Further optimization, such as device structure optimization, optimization for HTM, ETM and the combination of the host material, will further improve the performance of the device, especially the efficiency, drive voltage and life.

It is to be understood that the application of the present disclosure is not limited to the above-described examples and that a person skilled in the art may make improvement or modification in accordance with the above description, all of which are within the scope of the claims appended hereto.

What is claimed is:

1. An organic metal complex, represented by the following general formula (I) or (II):

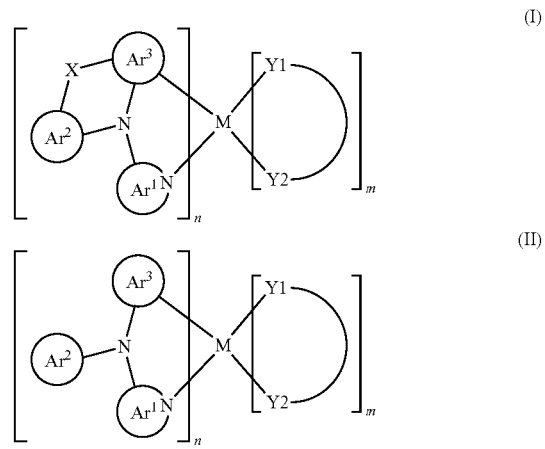

wherein,

X is a single bond, X is linked to Ar$^3$ or Ar$^2$ by a single bond;

each of Ar$^1$-Ar$^3$ is the same or different from one another in multiple occurrences, and is an unsubstituted or a R$^1$-substituted aromatic hydrocarbon or heteroaromatic cyclic hydrocarbon system;

each R$^1$ is the same or different from one another in multiple occurrences, and R$^1$ is selected from the group consisting of H; F; Cl; Br; I; D; CN; NO$_2$; CF$_3$; B(OR$^2$)$_2$; Si(R$^2$)$_3$; straight-chain alkanes; alkane ethers; alkane thioethers, branched alkanes or cycloalkanes containing 1 to 10 carbon atoms; and alkane ethers or alkane thioether groups containing 3 to 10 carbon atoms; each R$^1$ group is substituted with one or more active groups R$^2$, and one or more non-adjacent methylene groups (CH$_2$) are optionally substituted by any one selected from the group consisting of R$^2$C=CR$^2$, C=C, Si(R$^2$)$_2$, Ge(R$^2$)$_2$, Sn(R$^2$)$_2$, C=O, C=S, C=Se, C=N(R$^2$), O, S, —COO— and CONR$^2$; wherein one or more H can be substituted by D, F, Cl, Br, I, CN or N$_2$; or by an aromatic amine substituted by one or more R$^2$ or one aromatic or heteroaromatic group, or by a substituted or unsubstituted carbazole;

each R$^2$ is the same or different from one another in multiple occurrences, and is selected from the group consisting of H, D, an aliphatic alkane having 1 to 10 carbons atoms, an aromatic hydrocarbon, and a substituted or unsubstituted aromatic ring or heteroaromatic group having 5 to 10 carbon atoms;

is a single anion ligand, and is independently selected from the following general formulas in multiple occurrences:
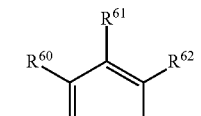 L1
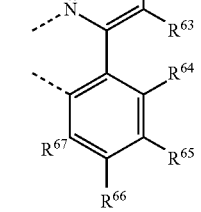 L2
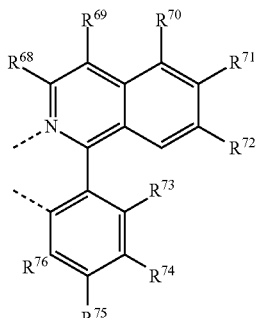 L3
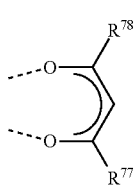 L4
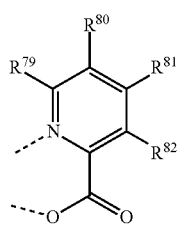 L5
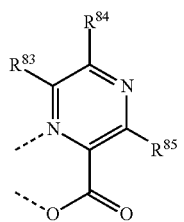 L6
-continued
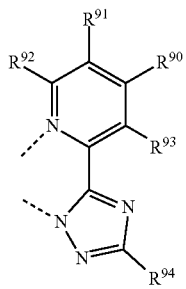 L7
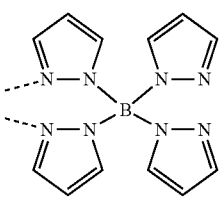 L8
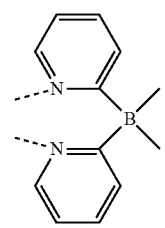 L9
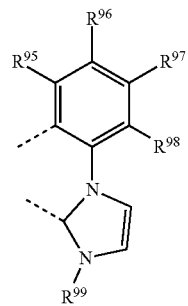 L10
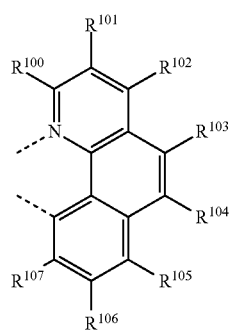 L11

-continued

L12
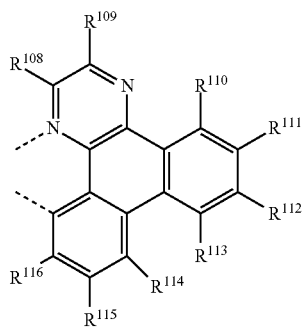

L14
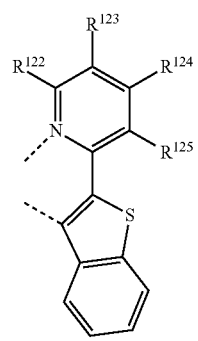

L15
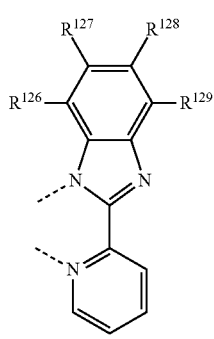

wherein each of $R^{60}$ to $R^{129}$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane or cycloalkane containing 1 to 10 carbon atoms; alkane ether or alkane thioether group containing 3 to 10 carbon atoms, and aryl group containing 6 to 10 carbon atoms, wherein the dashed line indicates connecting with the metal element M in the form of a single bond;

M is a transitional metal element;

m is any one of numbers 1-3, and n is any one of numbers 1-3.

2. The organic metal complex of claim 1, wherein the organic metal complex has a general formula selected from the group consisting of:

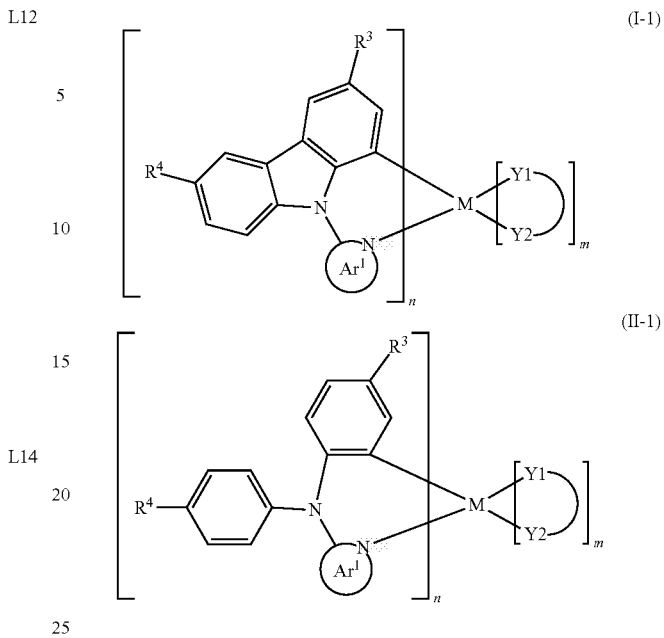

wherein each of $R^3$, and $R^4$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane, or cycloalkane containing 1 to 10 carbon atoms; alkane ether or alkane thioether group containing 3 to 10 carbon atoms; and aryl group containing 6 to 10 carbon atoms.

3. The organic metal complex of claim 1, wherein M is selected from the group consisting of Cr, Mo, W, Ru, Rh, Ni, Ag, Cu, Zn, Pd, Au, Os, Re, Ir and Pt.

4. The organic metal complex of claim 1, wherein M is selected from Ir or Pt.

5. The organic metal complex of claim 1, wherein

is N-hetero-six-membered ring unit, and is independently selected from general formulas C1 to C5 in multiple occurrences:

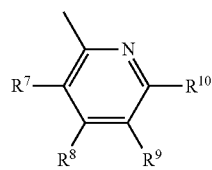

C1

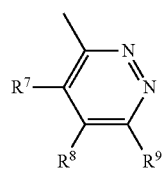

C2

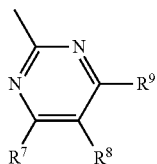

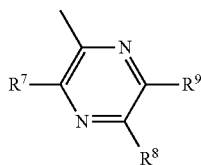

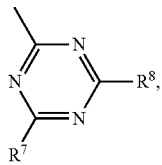

wherein each of $R^7$ to $R^{10}$ independently represents any one selected from the group consisting of —H; —F; —Cl; Br; I; -D; —CN; —NO$_2$; —CF$_3$; B(OR$^2$)$_2$; Si(R$^2$)$_3$; straight-chain alkane; alkane ether; alkane thioether, branched alkane or cycloalkane containing 1 to 10 carbon atoms; alkane ether or alkane thioether group containing 3 to 10 carbon atoms, and aryl group containing 6 to 10 carbon atoms.

6. The organic metal complex of claim 1, wherein the light emission wavelength is between 300 and 1000 nm.

7. A mixture comprising the organic metal complex of claim 1 and further at least one organic functional material which is any one selected from a hole-injecting material, a hole-transporting material, an electron-transporting material, an electron-injecting material, an electron-blocking material, a hole-blocking material, a light emitter material, and a host material.

8. The mixture of claim 7, comprising the organic metal complex with a weight percentage from 0.01 to 30 wt %.

9. The mixture of claim 7, further comprising a triplet host material.

10. The mixture of claim 7, further comprising a triplet host material and another organic metal complex.

11. A formulation comprising the organic metal complex of claim 1, and at least one organic solvent.

12. The formulation of claim 11, wherein the organic solvent is selected from the group consisting of methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxahexane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, naphthane, indene and/or a combination thereof.

13. The formulation of claim 11, wherein the formulation comprises the organic metal complex in weight percentage from 0.01 to 20%.

14. The formulation of claim 11, wherein the formulation comprises the organic metal complex in weight percentage from 0.01 to 15%.

15. The formulation of claim 11, wherein the formulation comprises the organic metal complex in weight percentage from 0.2 to 10%.

16. The formulation of claim 11, wherein the formulation comprises the organic metal complex in weight percentage from 0.25 to 5%.

17. The organic metal complex of claim 1, wherein the light emission wavelength is between 350 and 900 nm.

18. The organic metal complex of claim 1, wherein the light emission wavelength is between 400 and 800 nm.

19. The organic metal complex of claim 1, wherein M is Pt.

* * * * *